United States Patent [19]

Crawley et al.

[11] Patent Number: 5,089,495

[45] Date of Patent: Feb. 18, 1992

[54] HETEROCYCLIC THIAZOLE DERIVATIVES AND PHARMACEUTICAL COMPOSITIONS COMPRISING SAID DERIVATIVES

[75] Inventors: Graham C. Crawley, Oak Lane; Martin P. Edwards, Bollington, both of United Kingdom

[73] Assignees: Imperial Chemical Industries PLC, London; ICI Pharma, Cergy Cedex, France

[21] Appl. No.: 463,267

[22] Filed: Jan. 10, 1990

[30] Foreign Application Priority Data

Jan. 30, 1989 [FR] France ............... 89 4002518

[51] Int. Cl.[5] ............... A01N 43/58; A01N 43/40; C07D 401/12
[52] U.S. Cl. ............... 514/253; 514/269; 514/275; 514/333; 514/342; 544/238; 544/297; 544/298; 544/310; 544/336; 544/408; 544/409; 546/256; 546/280
[58] Field of Search ............... 546/280, 256; 544/238, 544/297, 298, 310, 311, 336, 408, 409; 514/253, 269, 275, 333, 342

[56] References Cited

FOREIGN PATENT DOCUMENTS 0110405 6/1984 European Pat. Off. .
0200101 12/1986 European Pat. Off. .
0219436 4/1987 European Pat. Off. .
8705510 9/1987 PCT Int'l Appl. .

*Primary Examiner*—C. Warren Ivy
*Assistant Examiner*—Raymond Covington
*Attorney, Agent, or Firm*—Cushman, Darby & Cushman

[57] ABSTRACT

The invention concerns a thiazole of the formula I,

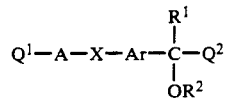

wherein $Q^1$ is an optionally substituted 6-membered monocyclic or 10-membered bicyclic heterocyclic moiety containing one or two nitrogen atoms;

X is oxy, thio, sulphinyl, sulphonyl or imino;

Ar is phenylene which may optionally bear one or two substituents, or

Ar is an optionally substituted 6-membered heterocyclene moiety continuing up to three nitrogen atoms;

$R^1$ is hydrogen, (1–6C)alkyl, (2–6C)alkenyl, (2–6C)alkynyl or substituted (1–4C)alkyl;

$R^2$ is hydrogen, (1–6C)alkyl, (3–6C)alkenyl, (3–6C)alkynyl or substituted (1–4C)alkyl or $R^2$ is optionally substituted benzoyl; and $Q^2$ is optionally substituted thiazolyl; or a pharmaceutically-acceptable salt thereof.

The invention also concerns processes for the manufacture of a thiazole of the formula I and pharmaceutical compositions containing said thiazole.

8 Claims, No Drawings

HETEROCYCLIC THIAZOLE DERIVATIVES AND PHARMACEUTICAL COMPOSITIONS COMPRISING SAID DERIVATIVES

This invention concerns novel heterocyclic derivatives and more particularly novel thiazoles which are inhibitors of the enzyme 5-lipoxygenase (hereinafter referred to as 5-LO). The invention also concerns processes for the manufacture of said thiazoles and novel pharmaceutical compositions containing said thiazoles. Also included in the invention is the use of said thiazoles in the treatment of various inflammatory and/or allergic diseases in which the direct or indirect products of 5-LO catalysed oxidation of arachidonic acid are involved, and the production of new medicaments for such use.

As stated above the thiazoles described hereinafter are inhibitors of 5-LO, which enzyme is known to be involved in catalysing the oxidation of arachidonic acid to give rise via a cascade process to the physiologically active leukotrienes such as leukotriene $B_4$ ($LTB_4$) and the peptido-lipid leukotrienes such as leukotriene $C_4$ ($LTC_4$) and leukotriene $D_4$ ($LTD_4$) and various metabolites.

The biosynthetic relationship and physiological properties of the leukotrienes are summarised by G. W. Taylor and S. R. Clarke in *Trends in Pharmacological Sciences*, 1986, 7, 100–103. The leukotrienes and their metabolites have been implicated in the production and development of various inflammatory and allergic diseases such as arthritic diseases, asthma, allergic rhinitis, atopic dermatitis, psoriasis, cardiovascular and cerebrovascular disorders and inflammatory bowel disease. In addition the leukotrienes are mediators of inflammatory diseases by virtue of their ability to modulate lymphocyte and leukocyte function. Other physiologically active metabolites of arachidonic acid, such as the prostaglandins and thromboxanes, arise via the action of the enzyme cyclooxygenase on arachidonic acid.

We have now discovered that certain thiazoles are effective as inhibitors of the enzyme 5-LO and thus of leukotriene biosyntheses. Thus, such compounds are of value as therapeutic agents in the treatment of, for example, allergic conditions, psoriasis, asthma, cardiovascular and cerebrovascular disorders, and/or inflammatory and arthritic conditions, mediated alone or in part by one or more leukotrienes.

According to the invention there is provided a thiazole of the formula I (set out hereinafter) wherein $Q^1$ is a 6-membered monocyclic or 10-membered bicyclic heterocyclic moiety containing one or two nitrogen atoms which may optionally bear one, two or three substituents selected from halogeno, hydroxy, oxo, cyano, (1–4C)alkyl, (1–4C)alkoxy, fluoro-(1–4C)alkyl, (1–4C)alkylamino-(1–4C)alkyl and di-[(1–4C)alkyl]amino-(1–4C)alkyl; wherein A is (1–6C)alkylene, (3–6C)alkenylene, (3–6C)alkynylene or cyclo(3–6C)alkylene; wherein X is oxy, thio, sulphinyl, sulphonyl or imino; wherein Ar is phenylene which may optionally bear one or two substituents selected from halogeno, hydroxy, amino, nitro, carboxy, cyano, carbamoyl, (1–4C)alkyl, (1–4C)alkoxy, (1–4C)alkylthio, (1–4C)alkylsulphinyl, (1–4C)alkylsulphonyl, (1–4C)alkylamino, di-[(1–4C)alkyl]amino, (1–4C)alkoxycarbonyl, N-[(1–4C)alkyl]carbamoyl, N,N-di-[(1–4C)alkyl]carbamoyl, (2–4C)alkanoylamino, hydroxy-(2–4C)alkoxy, (1–4C)alkoxy-(2–4C)alkoxy, amino-(2–4C)alkoxy, cyano-(1–4C)alkoxy, carbamoyl-(1–4C)alkoxy, N-[(1–4C)alkyl]carbamoyl-(1–4C)alkoxy, N,N-di-[(1–4C)alkyl]carbamoyl(1–4C)alkoxy, (1–4C)alkylamino-(2–4C)alkoxy, di-[(1–4C)alkyl]amino-(2–4C)alkoxy, (1–4C)alkoxycarbonyl-(1–4C)alkoxy, fluoro-(1–4C)alkyl, hydroxy-(1–4C)alkyl, amino-(1–4C)alkyl, cyano-(1–4C)alkyl, (1–4C)alkoxy-(1–4C)alkyl, (1–4C)alkylamino-(1–4C)alkyl, di-[(1–4C)alkyl]amino-(1–4C)alkyl and (2–4C)alkanoylamino-(1–4C)alkyl, or Ar is a 6-membered heterocylene moiety containing up to three nitrogen atoms which may optionally bear one or two substituents selected from halogeno, hydroxy, amino, cyano, (1–4C)alkyl, (1–4C)alkoxy, (1–4C)alkylamino and di-[(1–4C)alkyl]amino; wherein $R^1$ is hydrogen, (1–6C)alkyl, (2–6C)alkenyl, (2–6C)alkynyl, fluoro-(1–4C)alkyl, cyano-(1–4C)alkyl, hydroxy-(1–4C)alkyl, (1–4C)alkoxy-(1–4C)alkyl and (2–4C)alkanoyloxy-(1–4C)alkyl; wherein $R^2$ is hydrogen, (1–6C)alkyl, (3–6C)alkenyl, (3–6C)alkynyl, (1–4C)alkoxycarbonyl-(1–4C)alkyl, carboxy-(1–4C)alkyl, carbamoyl-(1–4C)alkyl, cyano(1–4C)alkyl or (2–4C)alkanoyl or $R^2$ is benzoyl which may optionally bear a substituent selected from halogeno, (1–4C)alkyl and (1–4C)alkoxy; and wherein $Q^2$ is thiazolyl which may optionally bear one or two substituents selected from halogeno, amino, nitro, cyano, carbamoyl, (1–4C)alkyl, (1–4C)alkoxy, (1–4C)alkylamino, di-[(1–4C)alkyl]amino, (1–4C)alkoxycarbonyl, N-[(1–4C)alkyl]carbamoyl, N,N-di-[(1–4C)alkyl]carbamoyl, (2–4C)alkanoylamino, fluoro-(1–4C)alkyl and hydroxy-(1–4C)alkyl; or a pharmaceutically-acceptable salt thereof.

The chemical formulae referred to herein by Roman numerals are set out for convenience on a separate sheet hereinafter.

In this specification the generic term "alkyl" includes both straight-chain and branched-chain alkyl groups. However references to individual alkyl groups such as "propyl" are specific for the straight-chain version only and references to individual branched-chain alkyl groups such as "isopropyl" are specific for the branched-chain version only. An analogous convention applies to other generic terms.

It is to be understood that, insofar as certain of the compounds of formula I defined above may exist in optically active or racemic forms by virtue of one or more substituents containing an asymmetric carbon atom, the invention includes in its definition of active ingredient any such optically active or racemic form which possesses the property of inhibiting 5-LO. The synthesis of optically active forms may be carried out by standard techniques of organic chemistry well known in the art, for example by synthesis from optically active starting materials or by resolution of a racemic form. Similarly, inhibitory properties against 5-LO may be evaluated using the standard laboratory techniques referred to hereinafter.

It is also to be understood that, insofar as certain of the compounds of the formula I as defined above may exhibit the phenomenon of tautomerism, for example a compound of the formula I wherein $Q^1$ bears an oxo or hydroxy substituent, and as any formula drawing presented herein may represent only one of the possible tautomeric forms the invention includes in its definition any tautomeric form of a compound of the formula I which possesses the property of inhibiting 5-LO and is not to be limited merely to any one tautomeric form utilised within the formulae drawings.

Suitable values for the generic terms referred to above include those set out below.

A suitable value for $Q^1$ when it is a 6-membered monocyclic or 10-membered bicyclic heterocyclic moiety containing one or two nitrogen atoms is, for example, pyridyl, pyridazinyl, pyrimidinyl, pyrazinyl, quinolyl, isoquinolyl, cinnolinyl, quinazolinyl, quinoxalinyl, phthalazinyl or naphthyridinyl, or a hydrogenated derivative thereof such as, for example, 1,2-dihydropyridyl or 1,2-dihydroquinolyl. The heterocyclic moiety may be attached through any available position including through any available nitrogen atom and it may bear a substituent on any available position including on any available nitrogen atom.

When $Q^1$ is a 10-membered bicyclic heterocyclic moiety containing one or two nitrogen atoms it will be appreciated that $Q^1$ may be attached to A from either of the two rings of the bicyclic heterocyclic moiety.

Conveniently $Q^1$ is, for example, 2-pyridyl, 3-pyridyl, 4-pyridyl, 3-pyridazinyl, 4-pyridazinyl, 2-pyrimidinyl, 4-pyrimidinyl, 5-pyrimidinyl, 2-pyrazinyl, 2-quinolyl, 3-quinolyl, 6-quinolyl, 7-quinolyl, 1-isoquinolyl, 3-isoquinolyl, 6-isoquinolyl, 7-isoquinolyl, 3-cinnolyl, 6-cinnolyl, 7-cinnolyl, 2-quinazolinyl, 4-quinazolinyl, 6-quinazolinyl, 7-quinazolinyl, 2-quinoxalinyl, 5-quinoxalinyl, 6-quinoxalinyl, 1-phthalazinyl, 6-phthalazinyl, 1,5-naphthyridin-2-yl, 1,5-naphthyridin-3-yl, 1,6-naphthyridin-3-yl, 1,6-naphthyridin-7-yl, 1,7-naphthyridin-3-yl, 1,7-naphthyridin-6-yl, 1,8-naphthyridin-3-yl, 2,6-naphthyridin-6-yl or 2,7-naphthyridin-3-yl.

A suitable value for a halogeno substituent which may be present on $Q^1$, Ar, $R^2$ or $Q^2$ is, for example, fluoro, chloro, bromo or iodo.

A suitable value for a (1–4C)alkyl substituent which may be present on $Q^1$, Ar, $R^2$ or $Q^2$ is, for example, methyl, ethyl, propyl, isopropyl, butyl, isobutyl or sec-butyl.

A suitable value for a (1–4C)alkoxy substituent which may be present on $Q^1$, Ar, $R^2$ or $Q^2$ is, for example, methoxy, ethoxy, propoxy, isopropoxy or butoxy.

A suitable value for a fluoro-(1–4C)alkyl substituent which may be present on $Q^1$, Ar or $Q^2$, or for $R^1$ when it is fluoro-(1–4C)alkyl, is, for example, fluoromethyl, difluoromethyl, trifluoromethyl, 2-fluoroethyl, 2,2,2-trifluoroethyl and pentafluoroethyl.

A suitable value for (1–4C)alkylamino-(1–4C)alkyl substituent which may be present on $Q^1$ is, for example, methylaminomethyl, 2-methylaminoethyl, 3-methylaminopropyl, ethylaminomethyl or 2-ethylaminoethyl; and for a di-[(1–4C)alkyl]amino-(1–4C)alkyl substituent is, for example, dimethylaminomethyl, 2-dimethylaminoethyl, 3-dimethylaminopropyl, diethylaminomethyl or 2-diethylaminoethyl.

A suitable value for A when it is (1–6C)alkylene is, for example, methylene, ethylene, ethylidene, trimethylene, propylidene, tetramethylene or pentamethylene; when it is (3–6C)alkenylene is, for example, 1-propenylene, 2-methylprop-1-enylene, 3-methylprop-1-enylene, 1-butenylene or 2-butenylene; and when it is (3–6C)alkynylene is, for example, 1-propynylene, 3-methylprop-1-ynylene, 1-butynylene or 2-butynylene.

A suitable value for A when it is cyclo(3–6C)alkylene is, for example, cyclopropylidene, 1,2-cyclopropylene, cyclopentylidene, 1,2-cyclopentylene, cyclohexylidene or 1,4-cyclohexylene.

A suitable value for Ar when it is phenylene is, for example, 1,3-phenylene or 1,4-phenylene.

A suitable value for Ar when it is a 6-membered heterocyclene moiety containing up to three nitrogen atoms is, for example, pyridylene, pyrimidinylene, pyridazinylene, pyrazinylene or 1,3,5-triazinylene. Conveniently Ar when it is a 6-membered heterocyclene moiety containing up to three nitrogen atoms is, for example, 2,4-, 2,5-, 3,5- or 2,6-pyridylene, 2,4-, 2,5- or 4,6-pyrimidinylene, 3,5- or 3,6-pyridazinylene or 2,5- or 2,6-pyrazinylene.

Suitable values for substituents which may be present on Ar include, for example:

| | |
|---|---|
| for (1-4C)alkythio: | methylthio, ethylthio, propylthio, isopropylthio and butylthio; |
| for (1-4C)alkylsulphinyl: | methylsulphinyl, ethylsulphinyl, propylsulphinyl, isopropylsulphinyl and butylsulphinyl; |
| for (1-4C)alkylsulphonyl: | methylsulphonyl, ethylsulphonyl, propylsulphonyl, isopropylsulphonyl and butylsulphonyl; |
| for (1-4C)alkylamino: | methylamino, ethylamino, propylamino and butylamino; |
| for di-[(1-4C)alkyl]amino: | dimethylamino, diethylamino and dipropylamino; |
| for (1-4C)alkoxycarbonyl: | methoxycarbonyl, ethoxycarbonyl and tert-butoxycarbonyl; |
| for N-[(1-4C)alkyl]carbamoyl: | N-methylcarbamoyl, N-ethylcarbamoyl and N-propylcarbamoyl; |
| for N,N-di-[(1-4C)alkyl]carbamoyl: | N,N-dimethylcarbamoyl and N,N-diethylcarbamoyl; |
| for (2-4C)alkanoylamino: | acetamido, propionamido and butyramido |
| for hydroxy-(2-4C)alkoxy: | 2-hydroxyethoxy and 3-hydroxypropoxy; |
| for (1-4C)alkoxy-(2-4C)alkoxy: | 2-methoxyethoxy, 3-methoxypropoxy and 2-ethoxyethoxy; |
| for amino-(2-4C)alkoxy: | 2-aminoethoxy and 3-aminopropoxy; |
| for cyano-(1-4C)alkoxy: | cyanomethoxy, 2-cyanoethoxy and 3-cyanopropoxy; |
| for carbamoyl-(1-4C)alkoxy; | carbamoylmethoxy, 2-carbamoylethoxy and 3-carbamoylpropoxy; |
| for [(1-4C)alkyl]amino-(2-4C)alkoxy: | 2-methylaminoethoxy, 3-methylaminopropoxy and 2-ethylaminoethoxy; |
| for di-[(1-4C)alkyl]amino-(2-4C)alkoxy: | 2-dimethylaminoethoxy, 3-dimethylaminopropoxy and 2-diethylaminoethoxy; |
| for (1-4C)alkoxycarbonyl-(1-4C)alkoxy: | methoxycarbonylmethoxy, 2-methoxycarbonylethoxy, ethoxycarbonylmethoxy and 2-ethoxycarbonylethoxy; |
| for N-[(1-4C)alkyl]carbamoyl-(1-4C)alkoxy: | N-methylcarbamoylmethoxy, 2-(N-methlcarbamoyl)ethoxy, N-ethylcarbamoylmethoxy and 2-(N-ethylcarbamoyl)ethoxy; |
| for N,N-di-[(1-4C)alkyl]carbamoyl-(1-4C)alkoxy: | N,N-dimethylcarbamoylmethoxy, 2-(N,N-dimethylcarbamoyl)ethoxy, N,N-diethylcarbamoylmethoxy and 2-(N,N-diethylcarbamoyl)ethoxy; |
| for hydroxy-(1-4C)alkyl: | hydroxymethyl, 1-hydroxyethyl, 2-hydroxyethyl, 1-hydroxypropyl, 2-hydroxypropyl and 3-hydroxypropyl; |
| for amino-(1-4C)alkyl: | aminomethyl, 2-aminoethyl and 3-aminopropyl; |
| for cyano-(1-4C)alkyl: | cyanomethyl, 2-cyanoethyl and 3-cyanopropyl; |
| for (1-4C)alkoxy-(1-4C)alkyl: | methoxymethyl, 2-methoxyethyl, 3-methoxypropyl, ethoxymethyl, 2-ethoxyethyl and 3-ethoxypropyl; |
| for (1-4C)alkylamino-(1-4C)alkyl: | methylaminomethyl, 2-methylaminoethyl, 3-methylaminopropyl, |

| | |
|---|---|
| for di-[(1-4C)alkyl]amino-(1-4C)alkyl: | ethylaminomethyl, 2-ethylaminoethyl and 3-ethylaminopropyl; dimethylaminomethyl, 2-dimethylaminoethyl, 3-dimethylaminopropyl, diethylaminomethyl, 2-diethylaminoethyl and 3-diethylaminopropyl; and |
| for (2-4C)alkanoylamino-(1-4C)alkyl: | acetamidomethyl, 2-acetamidoethyl, 3-acetamidopropyl, propionamidomethyl, 2-propionamidoethyl and 3-propionamidopropyl. |

A suitable value for $R^1$ when it is (1–6C)alkyl is, for example, methyl, ethyl, propyl, butyl, pentyl or hexyl; when it is (2–6C)alkenyl is, for example, vinyl, allyl, 2-butenyl or 3-butenyl; when it is (2–6C)alkynyl is, for example, ethynyl, 1-propynyl, 2-propynyl, 1-butynyl or 2-butynyl; when it is cyano-(1–4C)alkyl is, for example, cyanomethyl, 2-cyanoethyl or 3-cyanopropyl; when it is hydroxy-(1–4C)alkyl is, for example, hydroxymethyl, 2-hydroxyethyl or 3-hydroxypropyl; when it is (1–4C)alkoxy-(1–4C)alkyl is, for example, methoxymethyl, 2-methoxyethyl, 3-methoxypropyl, ethoxymethyl, 2-ethyoxyethyl or 3-ethoxypropyl; and when it is (2–4C)alkanoyloxy-(1–4C)alkyl is, for example, acetoxymethyl, 2-acetoxyethyl, 3-acetoxypropyl, propionyloxymethyl, 2-propionyloxyethyl or 3-propionyloxypropyl.

A suitable value for $R^2$ when it is (1–6C)alkyl is, for example, methyl, ethyl, propyl, iospropyl, butyl, isobutyl, sec-butyl, pentyl or hexyl; when it is (3–6C)alkenyl is, for example allyl, 2-butenyl or 3-butenyl; when it is (3–6C)alkynl is, for example 2-propynyl or 2butynyl; and when it is (2–4C)alkanoyl is, for example, acetyl, propionyl or butyryl. p A suitable value for $R^2$ When it is (1–6C)alkoxycarbonyl-(1–4C)alkyl is, for example, methoxycarbonylmethyl, 2-methoxycarbonylethyl, ethoxycarbonylmethyl or 2-ethoxycarbonylethyl; when it is carboxy-(1–4C)alkyl is, for example, carboxymethyl , 2-carboxyethyl or 3-carboxypropyl; when it is carbamoyl-(1–4C)alkyl is, for example, carbamoylmethyl, 2-carbamoylethyl or 3-carbamoylpropyl; and when it is cyano-(1–4C)alkyl is, for example, cyanomethyl, 2-cyanoethyl or 3-cyanopropyl.

A suitable value for $Q^2$ when it is thiazolyl is 2-, 4- or 5-thiazolyl.

Suitable values for substituent which many be present on $Q^2$ include, for example:

| | |
|---|---|
| for (1-4C)alkylamino: | methylamino, ethylamino, propylamino and butylamino; |
| for di-[(1-4C)alkyl]amino: | dimethylamino, diethylamino and dipropylamino; |
| for (1-4C)alkoxycarbonyl: | methoxycarbonyl, ethoxycarbonyl and tert-butoxycarbonyl; |
| for N-[(1-4C)alkyl]carbamoyl: | N-methylcarbamoyl, N-ethylcarbamoyl and N-propylcarbamoyl; |
| for N,N-di-[(1-4C)alkyl]-carbamoyl: | N,N-dimethylcarbamoyl and N,N-diethylcarbamoyl; |
| for (2-4C)alkanoylamino: | acetamido, propionamido and butyramido; and |
| for hydroxy-(1-4C)alkyl: | hydroxymethyl, 1-hydroxyethyl, 2-hydroxyethyl, 1-hydroxypropyl, 2-hydroxypropyl and 3-hydroxypropyl. |

A suitable pharmaceutically-acceptable salt of a thiazole of the invention which is sufficiently basic is an acid-addition salt with, for example, an inorganic or organic acid, for example hydrochloric, hydrobromic, sulphuric, phosphoric, trifluoroacetic, citric or maleic acid. In addition a suitable pharmaceutically-acceptable salt of a thiazole of the invention which is sufficiently acidic (for example a thiazole of the invention which contains a carboxy group) is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

Particular novel compounds of the invention are, for example, thiazoles of the formula I wherein:

(a) $Q^1$ is 2-pyridyl, 3-pyridyl, 3-pyridazinyl, 2-pyrimidinyl or 2-pyrazinyl which may optionally bear one substituent selected from chloro, hydroxy, cyano, methyl, methoxy and trifluoromethyl; and A, X, Ar, $R^1$, $R^2$ and $Q^2$ have any of the meanings defined hereinbefore;

(b) $Q^1$ is 2-pyridyl, 3-pyridyl, 4-pyridyl, 2-pyrimidinyl or 2-pyrazinyl; A is 1-propenylene or 1-propynylene; and X is oxy; and Ar, $R^1$, $R^2$ and $Q^2$ have any of the meanings defined hereinbefore;

(c) $Q^1$ is 2-quinolyl, 3-quinolyl, 6-quinolyl, 7-quinolyl, 3-isoquinolyl, 6-isoquinolyl, 7-isoquinolyl, 3-cinnolyl, 2-quinazolinyl 6 -quinazolinyl, 2-quinoxalinyl, 6-quinoxalinyl, 6-phthalazinyl, 1,7-naphthyridin-3-yl, 1 7-naphthyridin-6-yl, 1,8-naphthyridin-3-yl or 2,7-naphthyridin-3-yl which may optionally bear one or two substituents selected from chloro, hydroxy, oxo, cyano, methyl, methoxy and trifluoromethyl; and A, X, Ar, $R^1$, $R^2$ and $Q^2$ have any of the meanings defined hereinbefore;

(d) $Q^1$ is 1,2-dihydro-2-oxoquinolin-3-yl, 1,2-dihydro-2-oxoquinolin-6-yl, 1,2-dihydro-2-oxoquinolin-7-yl, 3,4-dihydro-4-oxoquinazolin-6-yl, 1,2-dihydro-2-oxo-1,7-naphthyridin-3-yl or 1,2-dihydro-2-oxo-1,8-naphthyridin-3-yl which may optionally bear one or two substituents selected from chloro, cyano, methyl, methoxy and trifluoromethyl; and A, X, Ar, $R^1$, $R^2$ and $Q^2$ have any of the meanings defined hereinbefore;

(e) $Q^1$ is 1,2-dihydro-2-oxoquinolin-3-yl or 1,2-dihydro-2-oxoquinolin-6-yl which may optionally bear one or two substitutes selected from fluoro, chloro, methyl, ethyl, methoxy, trifluoromethyl, 2-fluoroethyl and 2-dimethylaminoethyl; A is methylene; and X is oxy; and Ar, $R^1$, $R^2$ and $Q^2$ have any of the meanings defined hereinbefore;

(f) A is methylene, ethylene, trimethylene, 1-propenylene, 2-methylprop-1-enylene or 1-propynylene and $Q^1$, X, Ar, $R^1$, $R^2$ and $Q^2$ have any of the meanings defined hereinbefore;

(g) X is oxy and $Q^1$, A, Ar, $R^1$, $R^2$ and $Q^2$ have any of the meanings defined hereinbefore;

(h) Ar is 1,3-phenylene or 1,4-phenylene which may optionally bear one substituent selected from chloro, bromo, hydroxy, amino, nitro, methyl, methoxy, methylthio, methylsulphinyl, methylsulphonyl, methylamino, dimethylamino, trifluoromethyl, acetamido, cyanomethoxy and carbamoylmethoxy; and $Q^1$, A, X, $R^1$, $R^2$ and $Q^2$ have any of the meanings defined hereinbefore;

(i) Ar is 1,3-phenylene or 1,4-phenylene which may optionally bear one substituent selected from fluoro, chloro, hydroxy, amino, methoxy and trifluoromethyl; and $Q^1$, A, X, $R^1$, $R^2$ and $Q^2$ have any of the meanings defined hereinbefore;

(j) Ar is 2,4-, 2,5-, 3,5- or 2,6-pyridylene or 4,6-pyrimidinylene which may optionally bear one substituent selected from chloro, methyl and methoxy; and $Q^1$, A, X, $R^2$ and $Q^2$ have any of the meanings defined hereinbefore;

(k) Ar is 3,5-pyridylene; and $Q^1$, A, X, $R^1$, $R^2$ and $Q^2$ have any of the meanings defined hereinbefore;

(l) $R^1$ is hydrogen, methyl, ethyl, propyl, vinyl, ethynyl, 1-propynyl, trifluoromethyl, hydroxymethyl, methoxymethyl or acetoxymethyl; and $Q^1$, A, X, Ar, $R^2$ and $Q^2$ have any of the meanings defined hereinbefore;

(m) $R^1$ is methyl or ethyl; and $Q^1$, A, X, Ar, $R^2$ and $Q^2$ have any of the meanings defined hereinbefore;

(n) $R^2$ is hydrogen, methyl, ethyl, allyl, 2-propynyl or cyanomethyl; and $Q^1$, A, X, Ar, $R^1$ and $Q^2$ have any of the meanings defined hereinbefore; or (o) $R^2$ is methyl, ethyl or allyl; and $Q^1$, A, X, Ar, $R^1$ and $Q^2$ have any of the meanings defined hereinbefore;

(p) $Q^2$ is 2- or 4-thiazolyl; and $Q^1$, A, X, Ar, $R^1$ and $R^2$ have any of the meanings defined hereinbefore;

(q) $Q^2$ is 2-thiazolyl; and $Q^1$, A, X, Ar, $R^1$ and $R^2$ have any of the meanings defined hereinbefore;

or a pharmaceutically-acceptable salt thereof.

A particular compound of the invention comprises a thiazole of the formula I wherein $Q^1$ is pyridyl, pyrimidinyl, pyrazinyl, quinolyl, isoquinolyl, quinazolinyl or quinoxalinyl which may optionally bear one, two or three substituents selected from fluoro, chloro, hydroxy, oxo, methyl, ethyl, methoxy, trifluoromethyl, 2-fluoroethyl and 2-dimethylaminoethyl; wherein A is methylene, 1-propenylene or 1-propynylene; wherein X is oxy;

wherein Ar is 1,3-phenylene or 1,4-phenylene which may optionally bear one substituent selected from fluoro, chloro, hydroxy, amino, nitro, methyl, methoxy and trifluoromethyl, or Ar is 3,5-pyridylene;

wherein $R^1$ is methyl or ethyl;

wherein $R^2$ is hydrogen, methyl, ethyl or allyl; and $Q^2$ is 2-thiazolyl;

or a pharmaceutically acceptable salt thereof.

A further particular compound of the invention comprises a thiazole of the formula I wherein $Q^1$ is 2-pyridyl, 3-pyridyl, 3-pyridazinyl, 2-pyrimidinyl or 2-pyrazinyl which may optionally bear one substituent selected from chloro, hydroxy, cyano, methyl, methoxy and trifluoromethyl;

or $Q^1$ is 2-quinolyl, 3-quinolyl, 6-quinolyl, 7-quinolyl, 3-isoquinolyl, 6-isoquinolyl, 7-isoquinolyl, 3-cinnolyl, 2-quinazolinyl, 6-quinazolinyl, 2-quinoxalinyl, 6-quinoxalinyl, 6-phthalazinyl, 1,7-naphthyridin-3-yl, 1,7-naphthyridin-6-yl, 1,8-naphthyridin-3-yl or 2,7-naphthyridin-3-yl which may optionally bear one or two substituents selected from chloro, hydroxy, oxo, cyano, methyl, methoxy and trifluoromethyl;

or $Q^1$ is 1,2-dihydro-2-oxoquinolin-3-yl, 1,2-dihydro-2-oxoquinolin-6-yl, 1,2-dihydro-2-oxoquinolin-7-yl, 3,4-dihydro-4-oxoquinazolin-6-yl, 1,2-dihydro-2-oxo-1,7-naphthyridin-3-yl or 1,2-dihydro-2-oxo-1,8-naphthyridin-3-yl which may optionally bear one or two substituents selected from chloro, cyano, methyl, methoxy and trifluoromethyl;

wherein A is methylene, ethylene, trimethylene, 1-propenylene, 2-methylprop-1-enylene or 1-propynylene;

wherein X is oxy;

wherein Ar is 1,3-phenylene or 1,4-phenylene which may optionally bear one substituent selected from chloro, bromo, hydroxy, amino, nitro, methyl, methoxy, methylthio, methylsulphinyl, methylsulphonyl, methylamino, dimethylamino, trifluoromethyl, acetamido, cyanomethoxy and carbamoylmethoxy;

wherein Ar is 2,4-, 2,5-, 3,5- or 2,6-pyridylene or 4,6-pyrimidinylene which may optionally bear one substituent selected from chloro methyl and methoxy;

wherein $R^1$ is hydrogen, methyl, ethyl, propyl, vinyl, ethynyl, 1-propynyl, trifluoromethyl, hydroxymethyl, methoxymethyl or acetoxymethyl;

wherein $R^2$ is hydrogen, methyl, ethyl, allyl, 2-propynyl or cyanomethyl; and wherein $Q^2$ is 2-thiazolyl;

or a pharmaceutically-acceptable salt thereof.

A further preferred compound of the invention comprises a thiazole of the formula I wherein $Q^1$ is 2-quinolyl, 3-quinolyl, 6-quinolyl, 3-isoquinolyl, 2-quinazolinyl, 6-quinazolinyl, 6-quinoxalinyl, 1,2-dihydro-2-oxoquinolin-3-yl or 1,2-dihydro-2-oxoquinolin-6-yl which may optionally bear one or two substituents selected from fluoro, chloro, hydroxy, methyl and 2-dimethylaminoethyl;

wherein A is methylene;

wherein X is oxy;

wherein Ar is 1,3-phenylene or 1,4-phenylene which may optionally bear one substituent selected from fluoro and methoxy, or Ar is 3,5-pyridylene;

wherein $R^1$ is methyl or ethyl;

wherein $R^2$ is methyl; and wherein $Q^2$ is 2-thiazolyl;

or a pharmaceutically-acceptable salt thereof.

A preferred compound of the invention comprises a thiazole of the formula I wherein $Q^1$ is 2-pyridyl, 3-pyridyl, 4-pyridyl, 2-pyrimidinyl, 2-pyrazinyl or 1-isoquinolyl, wherein A is 1-propenylene or 1-propynylene;

wherein X is oxy;

wherein Ar is 1,3-phenylene or 1,4-phenylene which may optionally bear one substituent selected from fluoro and methoxy, or Ar is 3,5-pyridylene;

wherein $R^1$ is methyl or ethyl;

wherein $R^2$ is methyl; and wherein $Q^2$ is 2-thiazolyl;

or a pharmaceutically-acceptable salt thereof.

Specific especially preferred compounds of the invention include, for example, the following thiazoles of the formula I, or a pharmaceutically-acceptable salt thereof:

2-[1-[3-(3-isoquinolylmethoxy)phenyl]-1-methoxypropyl]thiazole,

2-[1-[3-(3-(2-pyridyl)prop-2-yn-1-yloxy)phenyl]-1-methoxypropyl]thiazole,

2-[1-[3-(3-(3-pyridyl)prop-2-yn-1-yloxy)phenyl]-1-methoxypropyl]thiazole,

2-[1-[3-(3-(3-pyridyl)prop-2-yn-1-yloxy)phenyl]-1-methoxyethyl]thiazole,

2-[1-methoxy-1-[3-methoxy-4-(quinol-2-ylmethoxy)-phenyl]propyl]thiazole,

2-[1-methoxy-1-[3-(1,2-dihydro-1-methyl-2-oxoquinolin-6-ylmethoxy)phenyl]propyl]thiazole, and
2-[1-[5-fluoro-3-(3-(2-pyridyl)prop-2-yn-1-yloxy)-phenyl]-1-methoxypropyl]thiazole.

A compound of the invention comprising a thiazole of the formula I, or a pharmaceutically-acceptable salt thereof, may be prepared by any process known to be applicable to the preparation of structurally-related compounds. Such procedures are provided as a further feature of the invention and are illustrated by the following representative examples in which, unless otherwise stated, $Q^1$, A, X, Ar, $R^1$, $R^2$ and $Q^2$ have any of the meanings defined hereinbefore.

(a) The alkylation, in the presence of a suitable reagent, of a compound of the formula II with a compound of the formula $Q^1$-A-Z wherein Z is a displaceable group; provided that, when there is an amino, alkylamino, hydroxy or carboxy group in $Q^1$, Ar, $R^1$, $R^2$ or $Q^2$, any amino, alkylamino or carboxy group is protected by a conventional protecting group and any hydroxy group may be protected by a conventional protecting group or alternatively any hydroxy group need not be protected; whereafter any undesired protecting group in $Q^1$, Ar, $R^1$, $R^2$ or $Q^2$ is removed by conventional means.

A suitable displaceable group Z is, for example, a halogeno, sulphonyloxy or hydroxy group, for example a chloro, bromo, iodo, methanesulphonyloxy or toluene-p-sulphonyloxy group.

A suitable reagent for the alkylation reaction when Z is a halogeno or sulphonyloxy group is, for example, a suitable base, for example, an alkali or alkaline earth metal carbonate, hydroxide or hydride, for example sodium carbonate, potassium carbonate, sodium hydroxide, potassium hydroxide, sodium hydride or potassium hydride. The alkylation reaction is preferably performed in a suitable inert solvent or diluent, for example N,N-dimethylformamide, N,N-dimethylacetamide, dimethylsulphoxide, acetone, 1,2-dimethoxyethane or tetrahydrofuran, and at a temperature in the range, for example, −10° to 150° C., conveniently at or near ambient temperature.

A suitable reagent for the alkylation reaction when Z is a hydroxy group is, for example, the reagent obtained when a compound of the formula $Q^1$—A—OH is reacted with a di-(1-4C)alkyl azodicarboxylate in the presence of a triarylphosphine, for example with diethyl azodicarboxylate in the presence of triphenylphosphine. The alkylation reaction is preferably performed in a suitable inert solvent or diluent, for example acetone, 1,2-dimethoxyethane or tetrahydrofuran, and at a temperature in the range, for example, 10° to 80° C., conveniently at or near ambient temperature.

A suitable protecting group for an amino or alkylamino group is, for example, an acyl group, for example a (1-4C)alkanoyl group, (especially acetyl), a (1-4C)alkoxycarbonyl group (especially methoxycarbonyl, ethoxycarbonyl or t-butoxycarbonyl), an arylmethoxycarbonyl group (especially benzyloxycarbonyl) or an aroyl group (especially benzoyl). The deprotection conditions for the above protecting groups necessarily vary with the choice of protecting group. Thus, for example, an acyl group such as an alkanoyl, alkoxycarbonyl or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid such as hydrochloric, sulphuric or phosphoric acid or trifluoroacetic acid, and an arylmethoxycarbonyl group such as a benzyloxycarbonyl group may be removed for example by hydrogenation over a catalyst such as palladium-on-charcoal.

A suitable protecting group for a carboxy group is, for example, an esterifying group, for example a (1-4C)alkyl group (especially methyl or ethyl) or an arylmethyl group (especially benzyl). The deprotection conditions for the above protecting groups necessarily vary with the choice of protecting group. Thus, for example, an esterifying group such as an alkyl or arylmethyl group may be removed, for example, by hydrolysis with a suitable base such as an alkali metal hydroxide, for example lithium or sodium hydroxide. Alternatively an esterifying group such as an arylmethyl group may be removed, for example, by hydrogenation over a catalyst such as palladium-on-charcoal.

A suitable protecting group for a hydroxy group is, for example, an acyl group, for example a (1-4C)alkanoyl group (especially acetyl), an aroyl group (especially benzoyl) or an arylmethyl group (especially benzyl). The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-charcoal.

The starting materials of the formula II may be obtained by standard procedures or organic chemistry. The preparation of examples of such starting materials is described within the accompanying non-limiting Examples which are provided for the purpose of illustration only. Other necessary starting materials are obtainable by analogous procedures to those described or by modification thereto which are within the ordinary skill of an organic chemist. Thus the starting material of the formula II may be obtained for example, by deprotecting a protected thiazole of the formula III wherein $R^3$ is a protecting group and X, Ar, $R^1$, $R^2$ and $Q^2$ have the meanings defined hereinbefore.

A suitable protecting group $R^3$ is, for example, an arylmethyl group (especially benzyl), a tri-(1-4C)alkylsilyl group (especially trimethylsilyl or t-butyldimethylsilyl), an aryldi-(1-4C)alkylsilyl group (especially dimethylphenylsilyl), a (1-4C)alkyl group (especially methyl, a (1-4C)alkoxymethyl group (especially methoxymethyl) or a tetrahydropyranyl group (especially tetrahydropyran-2-yl). The deprotection conditions for the above protecting groups will necessarily vary with the choice of protecting group. Thus, for example, an arylmethyl group such as a benzyl group may be removed, for example, by hydrogenation over a catalyst such as palladium-on-charcoal. Alternatively a trialkylsilyl or an aryl dialkylsilyl group such as a t-butyldimethylsilyl or a dimethylphenylsilyl group may be removed, for example, by treatment with a suitable acid such as hydrochloric, sulphuric, phosphoric or trifluoroacetic acid or with an alkali metal or ammonium fluoride such as sodium fluoride or, preferably, tetrabutylammonium fluoride. Alternatively an alkyl group may be removed, for example, by treatment with an alkali metal (1-4C)alkylsulphide such as sodium thioethoxide, for example, by treatment with an alkali metal diarylphosphide such as lithium diphenylphosphide or, for example, by treatment with a boron or aluminium trihalide such as boron tribromide. Alternatively a (1-4C)alkoxymethyl group or tetrahydropyranyl group may be removed, for example, by treatment with a suitable acid such as hydrochloric or trifluoroacetic acid.

The protecting group $R^3$ may be, for example, a tri-(1-4C)alkylsilyl group which can be removed while the protecting group for any amino, alkylamino, carboxy or hydroxy group in Ar, $R^1$, or $R^2$ or $Q^2$ is retained.

The protected starting material of the formula III may be obtained by standard procedures of organic chemistry as illustrated in the accompanying non-limiting Examples. Thus, for example, an alcohol of the formula $R^3$—X—Ar—CH(OH)—$Q^2$, wherein $R^3$ is a protecting group as defined hereinbefore, may be obtained by the reaction of an aldehyde of the formula $R^3$—X—Ar—CHO with an organometallic compound of the formula $Q^2$-M, wherein $Q^2$ has the meaning defined hereinbefore and M is a metallic group, for example lithium, and provided that any amino, alkylamino, carboxy or hydroxy group in Ar or $Q^2$ is protected by a conventional protecting group. The reaction may be carried out in, for example, a suitable solvent or diluent such as an ether (for example tetrahydrofuran t-butyl methyl ether or diethyl ether) at a temperature in the range, for example, $-100°$ to $25°$ C. (especially $-80°$ to $-50°$ C).

The secondary alcohol of the formula $R^3$—X—Ar—CH(OH)—$Q^2$ may be oxidised to give a ketone of the formula $R^3$—X—Ar—CO—$Q^2$. A particular suitable oxidising agent is, for example, any agent known in the art for the oxidation of a secondary alcohol to a ketone, for example, manganese dioxide, chromium trioxide pyridine complex, 2,3-dichloro-5,6-dicyano-1,4-benzoquinone (hereinafter DDO), a mixture of dimethylsulphoxide, oxalyl chloride and triethylamine, a mixture of acetic anhydride and dimethylsulphoxide or a mixture of dimethylsulphoxide and a dialkylcarbodiimide, for example N,N'-dicyclohexylcarbodiimide or N-ethyl-N'-(3-dimethylaminopropyl)-carbodiimide.

A tertiary alcohol of the formula IV, wherein $R^3$ has the meaning defined hereinbefore, may be obtained by the reaction of the ketone $R^3$—X—Ar—CO—$Q^2$ with an organometallic compound of the formula $R^1$—M—Z, wherein M is a metallic group, for example magnesium, and Z is a halogeno group, for example chloro, bromo or iodo, and provided that any amino, alkylamino, carboxy or hydroxy group in Ar, $R^1$ or $Q^2$ is protected by a conventional protecting group. The reaction may be carried out in a suitable solvent or diluent such as an ether (for example tetrahydrofuran, t-butyl methyl ether or diethyl ether) at a temperature in the range, for example, $-30°$ to $100°$ C. (especially ambient temperature to $80°$ C.).

It will be appreciated that the tertiary alcohol of the formula IV may be obtained from the aldehyde of the formula $R^3$—X—Ar—CHO by reversing the order of introduction of the groups $Q^2$ and $R^1$. Thus the aldehyde of the formula $R^3$—X—Ar—CHO may be treated initially with the organometallic compound of the formula $R^1$—M—Z, the product so obtained may be oxidised using a suitable oxidising agent as described above and the resultant ketone may be treated with the organometallic compound $Q^2$—M to give the compound of the formula IV, and provided that any amino, alkylamino, carboxy or hydroxy group in Ar, $R^1$ or $Q^2$ is protected by a conventional protecting group.

The protected thiazole of the formula III wherein $R^3$ has the meaning defined hereinbefore, may be obtained by the alkylation of the tertiary alcohol of the formula IV with an alkylating agent of the formula $R^2$—Z, wherein Z is a displaceable group as defined hereinbefore other than hydroxy, in the presence of a suitable base as defined hereinbefore, and provided that any amino, alkylamino, carboxy or hydroxy group in Ar, $R^1$, $R^2$ or $Q^2$ is protected by a conventional protecting group, Alternatively the tertiary alcohol of the formula IV may be obtained by the reaction of a compound of the formula $R^3$—X—Ar—Z, wherein $R^3$, X and Ar have the meanings defined hereinbefore and Z is a halogeno group as defined hereinbefore, and provided that any amino, alkylamino, hydroxy or carboxy group in Ar is protected with a conventional protecting group as defined hereinbefore, with either an organometallic compound of the formula $R^5$—M, wherein $R^5$ is a (1-6C)alkyl group such as butyl and M is a metallic group, for example lithium, to give an organometallic compound of the formula $R^3$—X—Ar—M, or with a metal such as magnesium to give an organometallic compound of the formula $R^3$—X—Ar—M—Z, whereafter either of these organometallic compounds may be reacted with a ketone of the formula $R^1$—CO—$Q^2$, wherein $R^1$ and $Q^2$ have the meanings defined herein before, and provided that any amino, alkylamino or hydroxy group in $R^1$ or $Q^2$ is protected by a conventional protecting group.

(b) The alkylation, in the presence of a suitable base as defined hereinbefore, of a compound of the formula V with a compound of the formula $R^2$—Z, wherein $R^2$ has the meaning defined hereinbefore and Z is a displaceable group as defined hereinbefore, provided that, when there is an amino, imino, alkylamino, hydroxy or carboxy group in $Q^1$, X, Ar, $R^1$, $R^2$ or $Q^2$, any amino, imino, alkylamino, hydroxy or carboxy group is protected by a conventional protecting group; whereafter any undesired protecting group in $Q^1$, X, Ar, $R^1$, $R^2$ or $Q^2$ is removed by conventional means.

A suitable protecting group for an imino group is, for example, any one of the protecting group defined hereinbefore as a suitable protecting group for an amino or alkylamino group.

The starting materials of the formula V may be obtained by standard procedures or organic chemistry. The preparation of examples of such starting materials is described within the accompanying non-limiting Examples which are provided for the purpose of illustration only. Other necessary starting materials are obtainable by analogous procedures to those described or by modification thereto which are within the ordinary skill of an organic chemist. Thus the tertiary alcohol starting material of the formula V may be obtained, for example, by the reaction of an aldehyde of the formula $Q^1$—A—X—Ar—CHO with an organometallic compound of the formula $Q^2$—M, having the meaning defined hereinbefore and using the conditions defined hereinbefore, to give a secondary alcohol of the formula $Q^1$—A—X—Ar—CH(OH)—$Q^2$ and provided that any amino, imino, alkylamino, carboxy or hydroxy group in $Q^1$, X, Ar or $Q^2$ is protected by a conventional protecting group. The product so obtained may be oxidised using a suitable oxidising agent, as defined hereinbefore, to give a ketone of the formula $Q^1$—A—X—Ar—CO—$Q^2$, which in turn may be treated with an organometallic compound of the formula $R^1$—M—Z, having the meaning defined hereinbefore, provided that any hydroxy group in $R^1$ is protected by a conventional protecting group, and using the conditions defined hereinbefore, to give the required tertiary alcohol starting material of the formula V.

It will be appreciated that the tertiary alcohol of the formula V may be obtained from the aldehyde of the formula $Q^1$—A—X—Ar—CHO by reversing the order of the introduction of the groups $Q^2$ and $R^1$, i.e. by reaction of the aldehyde of the formula $Q^1$—A—X—Ar—CHO with the organometallic compound of the formula $R^1$—M—Z, oxidation of the secondary alcohol to a ketone of the formula $Q^1$—A—X—Ar—CO—$R^1$ and reaction of said ketone with the organometallic compound of the formula $Q^2$—M, and provided that any amino, imino, alkylamino, carboxy or hydroxy group in $Q^1$, X, Ar, $R^1$ or $Q^2$ is protected by a conventional protecting group.

Alternatively the ketone intermediate of the formula $Q^1$—A—X—Ar—CO—$R^1$ may be obtained, for example, by the alkylation, in the presence of a suitable base as defined hereinbefore, of a ketone of the formula H—X—Ar—CO—$R^1$ with a compound of the formula $Q^1$—A—Z, wherein Z is a displaceable group as defined hereinbefore, and provided that any amino, alkylamino, carboxy or hydroxy group in $Q^1$, or $R^1$ is protected by a conventional protecting group.

The aldehyde starting material of the formula $Q^1$—A—X—Ar—CHO may be obtained, for example, by the alkylation, in the presence of a suitable base as defined hereinbefore, of an aldehyde of the formula H—X—Ar—CHO with a compound of the formula $Q^1$—A—Z, wherein Z is a displaceable group as defined hereinbefore other than hydroxy, and provided that any amino, alkylamino, carboxy or hydroxy group in $Q^1$ or Ar is protected by a conventional protecting group.

Alternatively the tertiary alcohol starting material of the formula V may be obtained, for example, by the reaction of an ester of the formula $Q^1$—A—X—Ar—CO $R^4$, wherein $R^4$ is a (1-4C)alkyl group such as methyl or ethyl, with an organometallic compound of the formula $Q^2$—M, having the meaning defined hereinbefore and using the conditions defined hereinbefore for the corresponding reaction of the aldehyde of the formula $R^3$—X—Ar—CHO, and provided that any amino, imino, alkylamino, carboxy or hydroxy group in $Q^1$, X, Ar or $Q^2$ is protected by a conventional protecting group, to give a ketone of the formula $Q^1$—A—X—Ar—CO—$Q^2$.

The product so obtained may be treated with an organometallic compound of the formula $R^1$—M—Z, having the meaning defined hereinbefore and using the conditions defined hereinbefore, to give the required tertiary alcohol starting material of the formula V.

It will be appreciated that the tertiary alcohol of the formula V may be obtained from the ester of the formula $Q^1$—A—X—Ar—$CO_2R^4$ by reversing the order of the introduction of the groups $Q^2$ and $R^1$, i.e. by reaction of the ester of the formula $Q^1$—A—X—Ar—CO $R^4$ with the organometallic compound of the formula $R^1$—M—Z, to give a ketone of the formula $Q^1$—A—X—Ar—CO—$R^1$ and reaction of said ketone with the organometallic compound of the formula $Q^1$—M, and provided that any amino, imino, alkylamino, carboxy or hydroxy group in $Q^1$, X, Ar, $R^1$ or $Q^2$ is protected by a conventional protecting group.

The ester starting material of the formula $Q^1$—A—X—Ar—$CO_2R^4$ may be obtained, for example, by the alkylation, in the presence of a suitable base as defined hereinbefore, of an ester of the formula H—X—Ar—$CO_2R^4$, wherein $R^4$ has the meaning defined hereinbefore, with a compound of the formula $Q^1$—A—Z, wherein Z is a displaceable group as defined hereinbefore other than hydroxy, and provided that any amino, alkylamino, carboxy or hydroxy group in $Q^1$ or Ar is protected by a conventional protecting group.

Alternatively the tertiary alcohol starting material of the formula V may be obtained, for example, by the alkylation, in the presence of a suitable base, of a compound of the formula $Q^1$—A—X—H, wherein $Q^1$, A and X have the meanings defined hereinbefore, with a compound of the formula Z—Ar—Z, wherein Z is a displaceable group as defined hereinbefore other than hydroxy, and provided that any amino, alkylamino, carboxy or hydroxy group in $Q^1$ or Ar is protected by a conventional protecting group, to give a compound of the formula $Q^1$—A—X—Ar—Z.

The product so obtained may be treated with an organometallic compound of the formula $R^5$—M, wherein $R^5$ is a (1-6C)alkyl group such as butyl and M is a metallic group, for example lithium, to give an organometallic compound of the formula $Q^1$—A—X—Ar—M which may be reacted with a ketone of the formula $Q^2.CO.R^1$, provided that any amino, alkylamino or hydroxy group in $Q^2$ or $R^1$ is protected by a conventional protecting group, to give the required tertiary alcohol starting material of the formula V.

(c) For the production of those compounds of the formula I wherein A is a (3-6C)alkynylene group, the coupling, in the presence of a suitable organometallic catalyst, of a heterocyclic compound of the formula $Q^1$—Z, wherein $Q^1$ has the meaning defined hereinbefore and Z is a halogeno group such as iodo, with an ethynyl compound of the formula VI, wherein $A^1$ is (1-4C)alkylene and X, Ar, $R^1$, $R^2$ and $Q^2$ have the meanings defined hereinbefore.

A suitable organometallic catalyst is, for example, any agent known in the art for such a coupling reaction. Thus, for example, a suitable reagent is formed when, for example, bis(triphenylphosphine)palladium chloride or tetrakis(triphenylphosphine)palladium, and a copper halide, for example cuprous iodide, are mixed. The coupling is generally carried out in a suitable inert solvent or diluent, for example acetonitrile, 1,2-dimethoxyethane, toluene or tetrahydrofuran, at a temperature in the range, for example, 10° to 80° C., conveniently at or near 70° C., and in the presence of a suitable base such as, for example, a tri-(1-4C)alkylamine such as triethylamine, or a cyclic amine such as piperidine.

The ethynyl compound of the formula VI, used as a starting material, may be obtained, for example, by the alkylation in the presence of a suitable base, of a compound of the formula II, wherein X, Ar, $R^1$, $R^2$ and $Q^2$ have the meanings defined hereinbefore, with an alkylating agent of the Formula H—C≡C—$A^1$—Z, wherein $A^1$ has the meaning defined hereinbefore and Z is a halogeno group, and provided that any amino, alkylamino, carboxy or hydroxy group in Ar, $R^1$, $R^2$ or $Q^2$ is protected by a conventional protecting group.

(d) For the production of those compounds of the formula I wherein Ar bears an alkylsulphinyl or alkylsulphonyl substituent or X is a sulphinyl or sulphonyl group, the oxidation of a compound of the formula I wherein Ar bears an alkylthio substituent or wherein X is a thio group.

A suitable oxidising agent is, for example any agent known in the art for the oxidation of thio to sulphinyl and/or sulphonyl, for hydrogen peroxide, a peracid (such as 3-chloroperoxybenzoic or peroxyacetic acid), an alkali metal peroxysulphate (such as potassium peroxymonosulphate), chromium trioxide or gaseous oxygen in the presence of platinum. The oxidation is generally carried out under as mild conditions as possible and with the required stoichiometric amount of oxidising agent in order to reduce the risk of over oxidation and damage to other functional groups. In general the reaction is carried out in a suitable solvent or diluent such as methylene chloride, chloroform, acetone, tetrahydrofuran or t-butyl methyl ether and at a temperature, for example, at or near ambient temperature, that is in the range 15° to 35° C. When a compound wherein X is sulphinyl and/or Ar bears an alkylsulphinyl substituent a milder oxidising agent may also be used, for example sodium or potassium metaperiodate, conveniently in a polar solvent such as acetic acid or ethanol. It will be appreciated that when a compound of the formula I containing a sulphonyl group is required, it may be obtained by oxidation of the corresponding sulphinyl compound as well as of the corresponding thio compound.

(e) For the production of those compounds of the formula I wherein $Q^1$, Ar or $Q^2$ bears an alkanoylamino or alkanoylaminoalkyl substituent, the acylation of a compound of the formula I wherein $Q^1$, Ar or $Q^2$ bears an amino or aminoalkyl substituent.

A suitable acylating agent is, for example, any agent known in the art for the acylation of amino to acylamino or of aminoalkyl to acylaminoalkyl, for example an acyl halide, for example a (2–6C)alkanoyl chloride or bromide, in the presence of a suitable base, an alkanoic acid anhydride, for example a (2–6C)alkanoic acid anhydride, or an alkanoic acid mixed anhydride, for example the mixed anhydride formed by the reaction of an alkanoic acid and a (1–4C)alkoxycarbonyl halide, for example a (1–4C)alkoxycarbonyl chloride, in the presence of a suitable base. In general the reaction is carried out in a suitable solvent or diluent such as methylene chloride, acetone, tetrahydrofuran or t-butyl methyl ether and at a temperature, for example, at or near ambient temperature, that is in the range 15° to 35° C. A suitable base when it is required is, for example, pyridine, 4-dimethylaminopyridine, triethylamine, ethyldiisopropylamine, N-methylmorpholine, an alkali metal carbonate, for example potassium carbonate, or an alkali metal carboxylate, for example sodium acetate.

(f) For the production of those compounds of the formula I wherein $R^2$ is alkanoyl or benzoyl optionally bearing a substituent as defined hereinbefore, the acylation of a compound of the formula I wherein $R^2$ is hydrogen. For the production of those compounds of the formula I wherein $R^2$ is alkanoyl the acylation reaction may be carried out using, for example, a suitable acylating agent as defined hereinbefore. For the production of those compounds of the formula I wherein $R^2$ is benzoyl optionally bearing a substituent the acylation may be carried out using, for example, a benzoyl halide, for example a benzoyl chloride or bromide, in the presence of a suitable base as defined hereinbefore.

(g) For the production of those compounds of the formula I wherein A is alkenylene or $R^1$ is alkenyl, the reduction of the corresponding compound wherein A is alkynylene or $R^1$ is alkynyl. In general conditions which are standard in the art for the reduction of an alkynyl or alkynylene group are used. Thus, for example, the reduction may be carried out by the hydrogenation of a solution of the alkynyl or alkynylene compound in an inert solvent or diluent in the presence of a suitable metal catalyst. A suitable inert solvent is, for example, an alcohol, for example methanol or ethanol, or an ether, for example tetrahydrofuran or t-butyl methyl ether. A suitable metal catalyst is, for example, palladium or platinum on an inert support, for example charcoal or barium sulphate.

Preferably a palladium-on-barium sulphate catalyst is used to substantially prevent over-reduction of the alkynyl or alkynylene group to an alkyl or alkylene group respectively. The reaction is generally carried out at a temperature at or near ambient temperature, that is in the range 15° to 35° C.

Alternatively the reduction may be carried out by treating a solution of the alkynyl or alkynylene compound in an inert solvent or diluent with a suitable mixture such as a 1:1 mixture of an organometallic hydride, for example a di-(1–6C)alkylaluminium hydride such as diisobutylaluminium hydride, and an alkyl metal, for example a (1–6C)alkyl lithium such as methyl lithium. A suitable inert solvent or diluent is, for example, tetrahydrofuran, diethyl ether or t-butyl methyl ether and, in general, the reaction is carried out at a temperature, for example, in the range −25° C. to ambient temperature (especially −10° to 10° C.).

(h) For the production of those compounds of the formula I wherein Ar bears an alkoxy or substituted alkoxy substituent, the alkylation of a compound of the formula I wherein Ar bears a hydroxy substituent.

A suitable alkylating agent is, for example any agent known in the art for the alkylation of hydroxy to alkoxy or substituted alkoxy, for example an alkyl or substituted alkyl halide, for example a (1–6C)alkyl chloride, bromide or iodide or a substituted (1–4C)alkyl chloride, bromide or iodide, in the presence of a suitable base. A suitable base for the alkylation reaction is, for example, an alkali or alkaline earth metal carbonate, hydroxide or hydride, for example sodium carbonate, potassium carbonate, sodium hydroxide, potassium hydroxide, sodium hydride or potassium hydride. The alkylation reaction is preferably performed in a suitable inert solvent or diluent, for example N,N-dimethylformamide, dimethylsulphoxide, acetone, 1,2-dimethoxyethane or tetrahydrofuran, and at a temperature in the range, for example, 20° to 150° C., conveniently at or near ambient temperature.

When a pharmaceutically-acceptable salt of a novel compound of the formula I is required, it may be obtained, for example, by reaction of said compound with a suitable acid or base using a conventional procedure. When an optically active form of a compound of the formula I is required, it may be obtained by carrying out one of the aforesaid procedures using an optically active starting material, or by resolution of a racemic form of said compound using a conventional procedure.

Many of the intermediates defined herein are novel, for example those of the formulae II, III, IV, V and VI and these are provided as a further feature of the invention.

As stated previously, the thiazoles of the formula I are inhibitors of the enzyme 5-LO. The effects of this inhibition may be demonstrated using one or more of the standard procedures set out below:

a) An in vitro spectrophotometric enzyme assay system, which assesses the inhibitory properties of a test compound in a cell free system using 5-LO isolated from guinea pig neutrophils and as described by D. Aharony and R. L. Stein (*J. Biol. Chem.*, 1986, 261(25), 11512–11519). This test provides a measure of the intrinsic inhibitory properties against soluble 5-LO in an extracellular environment.

b) An in vitro assay system involving incubating a test compound with heparinised human blood, prior to challenge with the calcium ionophore A23187 and then indirectly measuring the inhibitory effects on 5-LO by assaying the amount of $LTB_4$ using the specific radioimmunoassay described by Carey and Forder (F. Carey and R. A. Forder, *Brit. J. Pharmacol.* 1985, 84, 34P) which involves the use of a protein-$LTB_4$ conjugate produced using the procedure of Young et alia (*Prostaglandins*, 1983, 26(4),605–613). The effects of a test compound on the enzyme cyclooxygenase (which is involved in the alternative metabolic pathway for arachidonic acid and gives rise to prostaglandins, thromboxanes and related metabolites) may be measured at the same time using the specific radioimmunoassay for thromboxane $B_2(TxB_2)$ described by Carey and Forder (see above). This test provides an indication of the effects of a test compound against 5-LO and also cyclooxygenase in the presence of blood cells and proteins. It permits the selectivity of the inhibitory effect on 5-LO or cyclooxygenase to be assessed.

c) An ex vivo assay system, which is a variation of test b) above, involving administration of a test compound (usually orally as the suspension produced when a solution of the test compound in dimethylsulphoxide is added to carboxymethylcellulose), blood collection, heparinisation, challenge with A23187 and radioimmunoassay of $LTB_4$ and $TxB_2$. This test provides an indication of the bioavailability of a test compound as an inhibitor of 5-LO or cyclooxygenase.

d) An in vitro assay system involving the measurement of the inhibitory properties of a test compound against the liberation of $LTC_4$ and $PGE_2$ induced by zymosan on mouse resident peritoneal macrophages, using the procedure of Humes (J. L. Humes et alia, *Biochem. Pharmacol.*, 1983, 32, 2319–2322) and conventional radioimmunoassay systems to measure $LTC_4$ and $PGE_2$. This test provides an indication of inhibitory effects against 5-LO and cyclooxygenase in a non-proteinaceous system.

e) An in vivo system involving the measurement of the effects of a test compound in inhibiting the inflammatory response to arachidonic acid in the rabbit skin model developed by D. Aked et alia (*Brit. J. Pharmacol.*, 1986, 89, 431–438). This test provides an in vivo model for 5-LO inhibitors administered topically or orally.

f) An in vivo system involving measuring the effects of a test compound administered orally or intravenously on a leukotriene dependent bronchoconstriction induced by an antigen challenge in guinea pigs pre-dosed with an antihistamine (mepyramine), a $\beta$-adrenergic blocking agent (propranolol) and a cyclooxygenase inhibitor (indomethacin), using the procedure of W. H. Anderson et alia (*British J Pharmacology*, 1983, 78(1), 67–574). This test provides a further in vivo test for detecting 5-LO inhibitors.

Although the pharmacological properties of the compounds of the formula I vary with structural changes as expected, in general compounds of the formula I possess 5-LO inhibitory effects at the following concentrations or doses in one or more of the above tests a)–f):

| | |
|---|---|
| Test (a): | $IC_{50}$ in the range, for example, 0.1–30 micromolar; |
| Test (b): | $IC_{50}$ ($LTB_4$) in the range, for example, 0.1–40 micromolar, |
| | $IC_{50}$ ($TxB_2$) in the range, for example, 40–200 micromolar; |
| Test (c): | oral $ED_{50}$ ($LTB_4$) in the range, for example, 10–200 mg/kg; |
| Test (d): | $IC_{50}$ ($LTC_4$) in the range, for example, 0.001–1 micromolar, |
| | $IC_{50}$ ($PGE_2$) in the range, for example, 20–1000 micromolar; |
| Test (e): | inhibition of inflammation in the range, for example, 0.3–100 micrograms intradermally; |
| Test (f): | $ED_{50}$ in the range, for example, 0.5–10 mg/kg i.v. |

No overt toxicity or other untoward effects are present in tests c), e) and/or f) when compounds of the formula I are administered at several multiples of their minimum inhibitory dose or concentration.

Thus, by way of example the compound 2-[1-[3-(3-(2-pyridyl)prop-2-yn-1-yloxy)phenyl]-1-methoxypropyl]-thiazole has, an $IC_{50}$ of 0.7 micromolar against $LTB_4$ and of >40 micromolar against $TxB_2$ in test b), and an oral $ED_{50}$ of 50 mg/kg versus $LTB_4$ in test c). In general those compounds of the formula I which are particularly preferred have an $IC_{50}$ of <5 micromolar against $LTB_4$ and of >100 micromolar against $TxB_2$ in test b), and an oral $ED_{50}$ of <100 mg/kg against $LTB_4$ in test c).

These compounds are examples of thiazoles of the invention which show selective inhibitory properties for 5-LO as opposed to cyclooxygenase, which selective properties are expected to impart improved therapeutic properties for example, a reduction in or freedom from the gastrointestinal side-effects frequently associated with cyclooxygenase inhibitors such as indomethacin.

According to a further feature of the invention there is provided a pharmaceutical composition which comprises a thiazole of the formula I, or a pharmaceutically-acceptable salt thereof, in association with a pharmaceutically-acceptable diluent or carrier.

The composition may be in a form suitable for oral use, for example a tablet, capsule, aqueous or oily solution, suspension or emulsion; for topical use, for example a cream, ointment, gel or aqueous or oily solution or suspension; for nasal use, for example a snuff, nasal spray or nasal drops; for vaginal or rectal use, for example a suppository; for administration by inhalation, for example as a finely divided powder or a liquid aerosol; for sub-lingual or buccal use, for example a tablet or capsule; or for parenteral use (including intravenous, subcutaneous, intramuscular, intravascular or infusion), for example a sterile aqueous or oily solution or suspension. In general the above compositions may be prepared in a conventional manner using conventional excipients.

The amount of active ingredient (that is a thiazole formula I or a pharmaceutically-acceptable salt thereof) that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient.

According to a further feature of the invention there is provided a thiazole of the formula I, or a pharmaceutically-acceptable salt thereof, for use in a method of treatment of the human or animal body by therapy.

The invention also includes a method of treating a disease or medical condition mediated alone or in part by one or more leukotrienes which comprises administering to a warm-blooded animal requiring such treatment an effective amount of an active ingredient as defined above. The invention also provides the use of such an active ingredient in the production of a new medicament for use in a leukotriene mediated disease or medical condition.

The size of the dose for therapeutic or prophylactic purposes of a thiazole of the formula I will naturally vary according to the nature and severity of the conditions, the age and sex of the animal or patient and the route of administration, according to well known principles of medicine. As mentioned above, thiazoles of the formula I are useful in treating those allergic and inflammatory conditions which are due alone or in part to the effects of the metabolites of arachidonic acid arising by the linear (5-LO catalysed) pathway and in particular the leukotrienes, the production of which is mediated by 5-LO. As previously mentioned, such conditions include, for example, asthmatic conditions, allergic reactions, allergic rhinitis, allergic shock, psoriasis, atopic dermatitis, cardiovascular and cerebrovasular disorders of an inflammatory nature, arthritic and inflammatory joint disease, and inflammatory bowel diseases.

In using a compound of the formula I for therapeutic or prophylactic purposes it will generally be administered so that a daily dose in the range, for example, 0.5 mg to 75 mg per kg body weight is received, given if required in divided doses. In general lower doses will be administered when a parenteral route is employed. Thus, for example, for intravenous administration, a dose in the range, for example, 0.5 mg to 30 mg per kg body weight will generally be used. Similarly, for administration by inhalation, a dose in the range, for example, 0.5 mg to 25 mg per kg body weight will be used.

Although the compounds of the formula I are primarily of value as therapeutic agents for use in warm-blooded animals (including man), they are also useful whenever it is required to inhibit the enzyme 5-LO. Thus, they are useful as pharmacological standards for use in the development of new biological tests and in the search for new pharmacological agents.

By virtue of their effects on leukotriene production, the compounds of the formula I have certain cytoprotective effects for example they are useful in reducing or suppressing certain of the adverse gastrointestinal effects of the cyclooxygenase inhibitory nonsteroidal anti-inflammatory agents (NSAIA), such as indomethacin, acetylsalicylic acid, ibuprofen, sulindac, tolmetin and piroxicam. Furthermore, co-administration of a 5-LO inhibitor of the formula I with a NSAIA can result in a reduction in the quantity of the latter agent needed to produce a therapeutic effect, thereby reducing the likelihood of adverse side-effects. According to a further feature of the invention there is provided a pharmaceutical composition which comprises a thiazole of the formula I, or a pharmaceutically-acceptable salt thereof as defined hereinbefore, in conjunction or admixture with a cyclooxygenase inhibitory non-steroidal anti-inflammatory agent (such as mentioned above), and a pharmaceutically-acceptable diluent or carrier.

The cytoprotective effects of the compounds of the formula I may be demonstrated, for example in a standard laboratory model which assesses protection against indomethacin-induced or ethanol-induced ulceration in the gastrointestinal tract of rats.

The compositions of the invention may in addition contain one or more therapeutic or prophylactic agents known to be of value for the disease under treatment. Thus, for example a known platelet aggregation inhibitor, hypolipidemic agent, anti-hypertensive agent, beta-adrenergic blocker or a vasodilator may usefully also be present in a pharmaceutical composition of the invention for use in treating a heart or vascular disease or condition. Similarly, by way of example, an anti histamine, steroid (such as beclomethasone dipropionate), sodium cromoglycate, phosphodiesterase inhibitor or a beta-adrenergic stimulant may usefully also be present in a pharmaceutical composition of the invention for use in treating a pulmonary disease or condition.

The invention will now be illustrated in the following non-limiting Examples in which, unless otherwise stated:

(i) evaporations were carried out by rotary evaporations in vacuo and work-up procedures were carried out after removal of residual solids by filtration;

(ii) operations were carried out at room temperature, that is in the range 18°-20° C. and under an atmosphere of an inert gas such as argon;

(iii) column chromatography (by the flash procedure) and medium pressure liquid chromatography (MPLC) were performed on Merck Kieselgel silica (Art. 9385) obtained from E. Meck, Darmstadt, W. Germany;

(iv) yields are given for illustration only and are not necessarily the maximum attainable;

(v) the end-products of the formula I have satisfactory microanalyses and their structures were confirmed by NMR and mass spectral techniques;

(vi) intermediates were not generally fully characterised and purity was assessed by thin layer chromatographic, infra-red (IR) or NMR analysis; and (vii) melting points are uncorrected and were determined using a Mettler SP62 automatic melting point apparatus or an oil-bath apparatus; melting points for the end-products of the formula I were determined after recrystallisation from a conventional organic solvent such as ethanol, methanol, acetone, ether or hexane, alone or in admixture.

EXAMPLE 1

A mixture of 2-[1-(3-hydroxyphenyl)-1-methoxypropyl]thiazole (0.5 g, 2 mmol), 3-bromomethyl-1,2-dihydro-1-methylquinolin-2-one (0.5 g, 2 mmol), potassium carbonate (0.35 g, 2.5 mmol) and dimethylformamide (3 ml) was stirred at ambient temperature for 48 hours. The mixture was filtered, the filtrate was added to water (30 ml) and the mixture was extracted with elhyl acetate (3×15 ml). The organic extracts were combined, washed with a dilute aqueous sodium hydroxide solution and with a saturated sodium chloride solution dried (Na$_2$SO$_4$) and evaporated. The residue was purified by column chromatography eluting with toluene/ethyl acetate (7/3 v/v) to give 2-[1-methoxy-1-

[3-(1,2-dihydro-1-methyl-2-oxoquinolin-3-ylmethoxy)-phenyl]propyl]thiazole (0.84 g, 100%), m.p. 123°-125° C.

The thiazole starting material was obtained as follows:

A solution of 3-methoxyphenylmagnesium bromide in tetrahydrofuran (500 ml) was prepared from 3-methoxybromobenzene (187 g) and magnesium turnings (24 g) and was added over 1.5 hours to a mixture of propionic anhydride (260 g) and diethyl ether (500 ml) which had been cooled to −70° C. A saturated aqueous solution of ammonium chloride (500 ml) was added and the mixture was allowed to warm to ambient temperature. The organic layer was separated and washed in turn with a dilute aqueous sodium hydroxide solution and with a saturated aqueous sodium chloride solution. The organic layer was dried ($Na_2SO_4$) and evaporated to give 3-methoxypropiophenone as a yellow oil (160 g).

The product so obtained was added to hot pyridine hydrochloride [prepared by adding concentrated hydrochloric acid (272 ml) to pyridine (242 ml) and heating the mixture to distil off all of the water, which position was indicated when the boiling point of the distillate reached a temperature of 210° C.] and the temperature was maintained at 210° C. for 30 minutes. The mixture was poured onto ice. The yellow solid which was precipitated was filtered off, washed with water and dried. There was thus obtained 3-hydroxypropiophenone (125 g) which was used without further purification.

Tert-butyldimethylsilyl chloride (150 g) was added to a mixture of 3-hydroxypropiophenone (125 g), imidazole (142 g) and dimethylformamide (330 ml) and the mixture was stirred at ambient temperature for 16 hours. The mixture was poured into water (600 ml) and extracted with diethyl ether (600 ml). The organic layer was separated, washed with water (4×30 ml), dried ($Na_2SO_4$) and evaporated to give 3-(tert-butyldimethylsilyloxy)propiophenone as an oil (186 g, b.p. 114°-118° C. at 0.01 mm Hg).

A solution of the product so obtained (186 g) in diethyl ether (350 ml) vas added over 45 minutes to a cooled (−70° C.) solution of thiazol-2-yl-lithium [prepared by adding over 45 minutes a solution of 2-bromothiazole (66 ml) in diethyl ether (150 ml) to a mixture of n-butyl-lithium (1.6M in hexane, 460 ml) and diethyl ether (625 ml) which had been cooled to −70° C.]. The mixture was stirred and allowed to warm to ambient temperature and then a saturated aqueous ammonium chloride solution (500 ml) was added. The organic solution was separated, washed with a saturated aqueous sodium chloride solution, dried ($Na_2SO_4$) and evaporated. The was thus obtained 2-[1-(3-tert-butyldimethylsilyloxyphenyl)-1-hydroxypropylthiazole, as an oil (245 g), which was used without further purification.

A solution of the product so obtained (245 g) in tetrahydrofuran (500 ml) was added to a slurry of sodium hydride (55% w/w dispersion in oil, 30.6 g) in tetrahydrofuran (500 ml) and the mixture was stirred at ambient temperature for 16 hours. Methyl iodide (87 ml) was added and the mixture was stirred at ambient temperature for 2 hours. The mixture was poured into a saturated aqueous ammonium chloride solution (500 ml) and extracted with diethyl ether (3×400 ml). The combined extracts were washed with a saturated aqueous sodium chloride solution, dried ($Na_2SO_4$) and evaporated. There was thus obtained 2-[1-(3-tert-butyldimethylsilyloxyphenyl)-1-methoxypropyl]thiazole as a pale yellow oil (250 g).

A mixture oi the product so obtained (245 g), tetra-n-butylammonium fluoride (1M in tetrahydrofuran, 756 ml) and tetrahydrofuran (400 ml) was stirred at ambient temperature for 1 hour. The mixture was poured into a saturated aqueous ammonium chloride solution. The organic layer was separated, evaporated and redissolved in ethyl acetate (500 ml). The aqueous layer was extracted with ethyl acetate (2×250 ml). The organic solutions were combined, washed with a saturated aqueous ammonium chloride solution (250 ml) and with a saturated aqueous sodium chloride solution, dried ($Na_2SO_4$) and evaporated. The residue was recrystallised from a mixture of petrol (b.p. 60°-80° C.) and ethanol to give 2-[1-(3-hydroxyphenyl)-1-methoxypropyl]thiazole (129 g), m.p. 111°-113° C.

The 3-bromomethyl-1,2-dihydro-1-methylquinolin-2-one starting material was obtained as follows:

Sodium hydride (555 w/w suspension in oil; 0.268 g) was added portionwise to a stirred suspension of 1,2-dihydro-2-oxoquinoline-3-carbaldehyde (1 g) in dimethylformamide (10 ml) which had been cooled in an ice bath. The mixture was allowed to warm to ambient temperature and was then heated to 60° C. for 1 hour. The mixture was recooled in an ice bath and methyl iodide (0.41 ml) was added. Dimethylformamide (50 ml) was added and the mixture was stirred at ambient temperature for 16 hours. The mixture was poured into water (50 ml) and extracted with methylene chloride (3×50 ml). The combined extracts were washed with water (50 ml) and evaporated. The residue was triturated under diethyl ether to give 1,2-dihydro-1-methyl-2-oxoquinoline-3-carbaldehyde as a pale yellow solid (0.81 g, 74%).

The product so obtained was converted to 3-bromomethyl-1,2-dihydro-1-methylquinolin-2-one using the known procedure (*Chem. Pharm. Bull.*, 1985, 33, 3775) for the conversion of 1,2-dihydro-2-oxoquinoline-3-carbaldehyde to 3-bromomethyl-1,2-dihydroquinolin-2-one.

EXAMPLE 2

Using a similar procedure to that described in Example 1, except that the appropriate alkylating agent was used in place of 3-bromomethyl-1,2-dihydro-1-methylquinolin-2-one and the appropriate thiazole was used, there were obtained the compounds described in the following table:

TABLE I

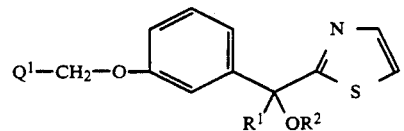

| Ex. 2 Compd. No. | $Q^1$ | $R^1$ | $R^2$ | Reaction Duration (hours) | Yield (%) | m.p. (°C.) |
|---|---|---|---|---|---|---|
| 1[a] | 1,2-dihydro-2-oxoquinolin-3-yl | Et | Me | 18 | 30 | 185 |
| 2[b] | 2-pyridyl | Et | Me | 18 | 55 | oil |
| 3[c] | 3-quinolyl | Et | Me | 96 | 67 | 102 |
| 4[d] | 6-quinolyl | Et | Me | 48 | 32 | 90 |
| 5[e] | 3-isoquinolyl | Et | Me | 24 | 30 | 94-95 |
| 6[f] | 6-quinoxalinyl | Et | Me | 24 | 32 | oil |
| 7[g] | 6-quinazolinyl | Et | Me | 18 | 35 | 83 |
| 8[h,i] | 2-pyridyl | Me | Me | 24 | 56 | 51 |

TABLE I-continued

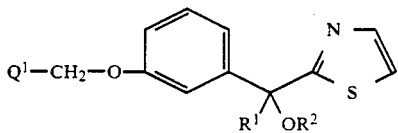

| Ex. 2 Compd. No. | $Q^1$ | $R^1$ | $R^2$ | Reaction Duration (hours) | Yield (%) | m.p. (°C.) |
|---|---|---|---|---|---|---|
| 9[f,h] | 6-quinoxalinyl | Me | Me | 24 | 47 | 95 |
| 10[j] | 2-quinolyl | Me | H | 24 | 67 | 47–49 |
| 11[k] | 2-quinolyl | Me | Me | 24 | 71 | 52–53 |
| 12[h] | 3-quinolyl | Me | Me | 96 | 48 | oil |

Notes a. 3-Bromomethyl-1,2-dihydroquinolin-2-one, used as a starting material, is described in *Chem. Pharm. Bull.*, 1985, 33, 3775.

b. 2-Chloromethylpyridine hydrochloride was used as the alkylating agent and three equivalents of potassium carbonate were used.

c. Three equivalents of potassium carbonate were used. 3-Chloromethylquinoline hydrochloride, used as a starting material, was prepared as follows:

A mixture of quinoline-3-carbaldehyde (5 g), formaldehyde (37% w/v solution in water, 8.6 ml), potassium hydroxide (5.5 g) and water (21 ml) was stirred at ambient temperature for 7 hours. The mixture was extracted with methylene chloride (2×20 ml) and the combined extracts were dried ($Na_2SO_4$) and evaporated. There was thus obtained 3-hydroxymethylquinoline (3.3 g after recrystallisation from toluene). A solution of a portion (3 g) of this product in methanol was cooled in an ice-bath and a saturated solution of hydrogen chloride in diethyl ether was added giving precipitation of 3-hydroxymethylquinoline hydrochloride which was filtered off and washed with diethyl ether.

A mixture of the product so obtained and thionyl chloride was heated to reflux for 3 hours. The mixture was evaporated, toluene was added and the mixture was re-evaporated. The residue was triturated in diethyl ether to give 3-chloromethylquinoline hydrochloride as a fawn solid (4.12 g).

d. Three equivalents of potassium carbonate were used. 6-Chloromethylquinoline hydrochloride, used as a starting material, was prepared as follows:

A mixture of 4 aminobenzoic acid (27.5 g), 4-nitrobenzoic acid (21.3 g), ferrous sulphate (7 g), boric acid (12 g), glycerol (75 ml) and concentrated sulphuric acid (35 ml) was heated to reflux for 20 hours.

The mixture was diluted with water (200 ml) and basified by adding a 5N aqueous sodium hydroxide solution. The mixture was filtered and the filtrate was acidified to pH 4–5 by adding glacial acetic acid. The mixture was stored at 0° C. for 2 hours. The precipitate was isolated by filtration, washed with water and with acetone, and dried by heating to 55° C. in vacuo. There was thus obtained quinoline-6-carboxylic acid (78 g), m.p. 286° C.

A mixture of the product so obtained, ethanol (600 ml) and concentrated sulphuric acid (96 ml) was heated to reflux for 5 hours. The bulk of the ethanol was evaporated. Water (200 ml) was added and the mixture was basified by adding a 5N aqueous sodium hydroxide solution. The mixture was extracted with chloroform (3×100 ml). The combined extracts were dried ($Na_2SO_4$) and evaporated. There was thus obtained ethyl quinoline-6-carboxylate (17 g, b.p. 140°–145° C. at 0.05 mm Hg).

A solution of the product so obtained in diethyl ether (100 ml) was added to a mixture of lithium aluminium hydride (3.6 g) and diethyl ether (200 ml) at a rate sufficient to heat the mixture to a gentle reflux. The mixture was then heated to reflux for 20 minutes. Wet ether (100 ml) was added carefully then aqueous sodium hydroxide solution [4.6 g in water (30 ml)] was added. The mixture was filtered and the solid was washed with diethyl ether. The combined filtrate and washings were washed with a saturated aqueous sodium chloride solution, dried ($Na_2SO_4$) and evaporated. There was thus obtained 6-hydroxymethylquinoline [7 g, recrystallised from a mixture of petroleum ether (b.p. 60°–80° C.) and diethyl ether].

The product so obtained was treated in turn with hydrogen chloride and with thionyl chloride using the procedures described in Note c above for the conversion of 3-hydroxymethylquinoline to 3-chloromethylquinoline hydrochloride. There was thus obtained 6-chloromethylquinoline hydrochloride.

e. Three equivalents of potassium carbonate were used. 3-Chloromethylisoquinoline hydrochloride, used as a starting material, was obtained as follows:

A mixture of phenylalanine (40 g), formaldehyde (37% w/v in water, 91 ml) and concentrated hydrochloric acid (310 ml) was stirred and heated to reflux for 4 hours and then stored at ambient temperature for 16 hours. The precipitate was filtered off, washed with cold water and with acetone to give 1,2,3,4-tetrahydroisoquinoline-3-carboxylic acid (11 g).

A mixture of this product (11 g), potassium acetate (19.6 g) and dry ethanol (200 ml) was heated to reflux and a solution of iodine (25.4 g) in dry ethanol (250 ml) was added over a period of 3 hours to the heated mixture. The mixture was heated to reflux for 16 hours, cooled and filtered and the filtrate was evaporated. The residue was partitioned between ethyl acetate and a dilute aqueous sodium thiosulphate solution.

The organic layer was dried ($Na_2SO_4$) and evaporated. The residue was purified by column chromatography eluting with ethyl acetate to give ethyl isoquinoline-3-carboxylate (3 g).

Di-isobutylaluminium hydride (1.5M in toluene, 13.2 ml) was added dropwise to a mixture of the product so obtained (3.5 g) and dry tetrahydrofuran (100 ml) which had been cooled to −70° C. and the mixture was stirred at this temperature for 30 minutes. The mixture was allowed to warm to ambient temperature, a saturated aqueous ammonium chloride solution was added and the mixture was extracted with methylene chloride (3×100 ml). The combined extracts were dried ($Na_2SO_4$) and evaporated to give isoquinoline-3-carbaldehyde (2.7 g) as a brown crystalline solid.

The product so obtained was reduced to 3-hydroxymethylisoquinoline which was converted to 3-chloromethylisoquinoline hydrochloride using the procedures described in Note c. above for the conversion of quinoline-3-carbaldehyde to 3-chloromethylquinoline hydrochloride.

f. 6-Bromomethylquinoxaline, used as a starting material, is described in *J. Het. Chem.*, 1974, 11, 595.

g. 6-Bromomethylquinazoline, used as a starting material, was prepared from 6-methylquinazoline (*J. Chem. Soc.*, 1962, 561) using the procedure described in

*J. Het Chem.*, 1974, 11, 595 for the preparation of 6-bromomethylquinoxaline from 6-methylquinoxaline.

h. 2-[1-(3-Hydroxyphenyl)-1-methoxyethyl]thiazole, m.p. 158°-160° C., used in place of 2-[1-(3-hydroxyphenyl)-1-methoxypropyl]thiazole, was prepared from 3-hydroxyacetophenone using the procedure described in the portion of Example 1 concerned with the preparation of starting materials for the conversion of 3-hydroxypropiophenone to 2-[1-(3-hydroxyphenyl)-1-methoxypropyl]thiazole.

i. 2-Chloromethylpyridine hydrochloride was used as the alkylating agent and three equivalents of potassium carbonate were used.

j. 2-[1-Hydroxy-(3-hydroxyphenyl)ethyl]thiazole used as the appropriate thiazole was obtained by the treatment of 2-[1-(3-tert-butyldimethylsilyloxyphenyl)-1-hydroxyethylthiazole [one of the intermediates in the preparation described in Note h. above] with tetra-n-butylammonium fluoride (1M in tetrahydrofuran) using the procedure described in the 6th paragraph of the portion of Example 1 which is concerned with the preparation of starting materials.

k. This compound was obtained by the methylation of the preceding compound in Table I using the procedure described in the 5th paragraph of the portion of Example 1 which is concerned with the preparation of starting materials. The product was purified by column chromatography eluting with toluene/ethyl acetate (4/1 v/v).

EXAMPLE 3

Diethyl azodicarboxylate (0.38 ml) was added dropwise to a mixture of 2-[1-(3 hydroxyphenyl)-1-methoxypropyl]thiazole (0.37 g), triphenylphosphine (0.57 g), 3-(3-pyridyl)prop-2-en-1-ol (0.27 g) and tetrahydrofuran (7 ml) which had been cooled to 0°-5° C. in an ice-bath. The mixture was stirred at this temperature range for 2 hours and then at ambient temperature for 4 hours. Further portions of diethyl azodicarboxylate (0.1 ml), triphenylphosphine (0.14 g) and the propenol (0.045 g) were added and the mixture was stirred at ambient temperature for 18 hours. The mixture was partitioned between ethyl acetate (40 ml) and dilute aqueous hydrochloric acid (40 ml). The aqueous layer was separated and basified by adding potassium carbonate portionwise. The resulting solution was extracted with ethyl acetate (3×20 ml). The combined extracts were dried ($Na_2SO_4$) and evaporated. The residue was purified by column chromatography eluting with toluene/ethyl acetate (2/3 v/v) to give 2-[1-[3-(3-pyridyl)prop-2-en-1-yloxy)phenyl[-1-methoxypropyl-thiazole as a colourless oil (0.162 g).

3-(3-Pyridyl)prop-2-en-1-ol, used as a starting material, was obtained as follows:-

Triethylamine (1.4 ml) and ethyl chloroformate (0.94 ml) were added in succession to a stirred suspension of 3-(3-pyridyl)propenoic acid [1.49 g; prepared from pyridine-3-carbaldehyde and malonic acid using the general method described in *Organic Synthesis*, Coll, Vol. 4, 1963, 730] in tetrahydrofuran (40 ml) which had been cooled to −15° C. The mixture was stirred at this temperature for 30 minutes and then filtered. The filtrate was added over 15 minutes to a stirred solution of sodium borohydride (0.94 g) in water (8 ml) which had been cooled in an ice-bath. The mixture was stirred at ambient temperature for 3 hours then partitioned between diethyl ether and a dilute aqueous sodium hydroxide solution. The aqueous layer was extracted with diethyl ether and ethyl acetate. The combined organic extracts were washed with a saturated aqueous sodium chloride solution, dried ($Na_2SO_4$) and evaporated. The residue was purified by column chromatography eluting with toluene/ethyl acetate (1/1 v/v) to give 3-(3-pyridyl)prop-2-en-1-ol as an oil (0.84 g).

EXAMPLE 4

The procedure described in Example 3 was repeated except that 3-(2-pyridyl)prop-2-en-1-ol was used in place of 3-(3-pyridyl)prop-2-en-1-ol. There was thus obtained 2-[1-[3-(3-(2-pyridyl)prop-2-en-1-yloxy)-phenyl]-1-methoxypropyl]thiazole as an oil.

3-(2-Pyridyl)prop-2-en-1-ol used as a starting material was obtained using the procedure described in the portion of Example 3 which is concerned with the preparation of starting materials and replacing pyridine-3-carbaldehyde with pyridine-2-carbaldehyde.

EXAMPLE 5

A solution of 2-[1-(3-(2-propynyloxy)phenyl)-1methoxypropyl]thiazole (8.6 g) in acetonitrile (40 ml) was added to a stirred mixture of 2-iodopyridine (6.2 g), triethylamine (4.02 ml), bis(triphenylphosphine)palladium chloride (0.416 g), cuprous iodide (0.416 g) and acetonitrile (160 ml), the mixture was stirred at ambient temperature for 15 minutes, and then heated to 60° C. for 2.5 hours. The mixture was cooled to ambient temperature and partitioned between diethyl ether and water. The organic layer was washed with a saturated aqueous sodium chloride solution, dried ($MgSO_4$) and evaporated. The residue was partitioned between diethyl ether and 2N aqueous hydrochloric acid. The aqueous layer was cooled to 10° C. in an ice-bath, basified by adding 4N aqeuous sodium hydroxide solution and extracted with diethyl ether (2×150 ml). The combined extracts were washed with water, dried ($MgSO_4$) and evaporated. There was thus obtained, as an oil which crystallised on standing and was recrystallised from diethyl ether, 2-[1-[3-(3-(2-pyridyl)prop-2-yn-1-yloxy)phenyl]-1-methoxypropyl]thiazole (5 g, 46%), m.p. 61°-63° C.

The 2-[1-(3-(2-propynyloxy)phenyl)-1-methoxypropyl]thiazole, used as a starting material, was obtained as follows:

A mixture of 2-[1-(3-hydroxyphenyl)-1-methoxypropyl]thiazole (31 g), 2-propynyl bromide (80% solution in toluene, 48.1 ml), potassium carbonate (48 g) and acetone (375 ml) was stirred and heated to reflux for 17 hours. The mixture was filtered and the filtrate was evaporated. The residue was partitioned between diethyl ether and water and the organic layer was washed with water, dried ($MgSO_4$) and evaporated. The residue was purified by chromatography eluting with hexane/ethyl acetate (1:1 v/v) to give 2-[1-(3-(2-propynyloxy)phenyl)-1-methoxypropyl]thiazole as an oil (34 g, 94%).

EXAMPLE 6

Using a similar procedure to that described in Example 5, except that the appropriate iodo-heterocycle was used in place of 2-iodopyridine and the appropriate thiazole was used, there were obtained the compounds described in the following table:

TABLE II

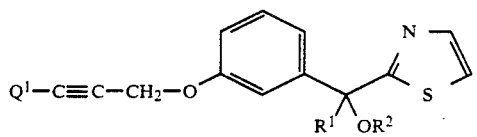

| Ex. 6 Compd. No. | Q¹ | R¹ | R² | Reaction Duration (hours) | Yield (%) | m.p. (°C.) |
|---|---|---|---|---|---|---|
| 1 | pyrazinyl | Et | Me | 2.5 | 38 | oil |
| 2[a,b] | 3-pyridyl | Me | Me | 0.5 | 24 | 61–62 |
| 3[a,b] | pyrazinyl | Me | Me | 0.5 | 50 | oil |
| 4[a,b] | 2-pyrimidinyl | Me | Me | 0.5 | 25 | 67–68 |

Notes
[a] 2-[1-(3-Hydroxyphenyl)-1-methoxyethyl]thiazole was used as a starting material.
[b] The reaction mixture was partitioned between ethyl acetate and water and the residue isolated from the organic layer was purified by column chromatography eluting with mixtures of hexane and ethyl acetate.

EXAMPLE 7

A mixture of 2-[1-(3-hydroxyphenyl)-1-methoxypropyl]thiazole (0.25 g), potassium carbonate (0.28 g), 3-(3-pyridyl)prop2-yn-1-yl bromide hydrobromide (0.28 g) and acetone (5 ml) was stirred and heated to reflux for 17 hours. The mixture was cooled to ambient temperature, filtered and the filtrate was evaporated. The residue was purified by column chromatography eluting with hexane/ethyl acetate (1:1 v/v) to give 2-[1-[3-(3-(3-pyridyl)prop-2-yn-1-yloxy)phenyl]-1-methoxypropyl]thiazole as an oil (0.217 g, 59%).

The 3-(3-pyridyl)prop-2-yn-1-yl bromide hydrobromide used as a starting material was obtained as follow:

2-Propynyl alcohol (2.1 g) was added dropwise to a stirred mixture of 3-iodopyridine (2.2 g), bis(triphenylphosphine)palladium chloride (0.1 g), triethylamine (1.4 ml), cuprous iodide (0.1 g) and acetonitrile (10 ml) and the mixture was stirred at ambient temperature for 30 minutes and the heated to 60° C. for 2 hours. The mixture was cooled to ambient temperature, poured into water (100 ml) and neutralised by adding dilute aqueous hydrochloric acid. The mixture was extracted with diethyl ether (2×100 ml) and the combined extracts were washed with water (100 ml), dried (MgSO₄) and evaporated. The residue was purified by column chromatography eluting with methylene chloride to give 3-(3-pyridyl)prop-2-yn-1-yl alcohol (0.8 g), m.p. 99°–100° C.

A solution of bromine (0.8 g) in methylene chloride (3 ml) was added to a mixture of triphenylphosphine (1.73 g) and methylene chloride (18 ml) which had been cooled to 5° C. in an ice-bath. A solution of the alcohol (0.8 g) obtained immediately above in methylene chloride (20 ml) was added and the mixture was stirred for 10 minutes and cooled to approximately 8° C. The mixture was filtered to give 3-(3-pyridyl)prop-2-yn-1-yl bromide hydrobromide (1.05 g, 63%), m.p. 158°–160° C., which was used without further purification.

EXAMPLE 8

A mixture of 2-[1-hydroxy-1-(3-hydroxyphenyl)-2,2,2-trifluoroethyl]thiazole (0.33 g), 2-chloromethylquinoline hydrochloride (0.22 g), potassium carbonate (0.5 g) and dimethylformamlde (5 ml) was stirred at ambient temperature for Z4 hours. The mixture was partitioned between ethyl aceiate and water and the organic layer was separated, washed with a saturated aqueous sodium chloride solution, dried (MgSO₄) and evaporated. The residue was purified by column chromatography eluting with chloroform/ethyl acetate (9/1 v/v) to give 2-[1-hydroxy-1-[3-(quinol-2-ylmethoxy)-phenyl]-2,2,2-trifluoroethyl]thiazole (0.15 g, 30%), m.p. 177° C.

The 2-[1-hydroxy-1 (3-hydroxyphenyl)-2,2,2-trifluoroethyl]thiazole used as a starting material was obtained as follows:

A solution of 3-methoxy-α,α,α-trifluoroacetophenone (1 86 g) in tetrahydrofuran (10 ml) was added dropwise to a cooled (−60° C.) solution of thiazol-2-yl-lithium [prepared by adding a solution of n-butyl-lithium (1.46M in hexane, 6.8 ml) to a mixture of thiazole (1 ml) and tetrahydrofuran (10 ml) which had been cooled to −60° C.]. The mixture was allowed to warm to ambient temperature and was stirred for 18 hours. The mixture vas partitioned between ethyl acetate and a saturated aqueous ammonium chloride solution. The organic layer was washed with water and with a saturated aqueous sodium chloride solution, dried (MgSO₄) and evaporated. The solid residue was recrystallised from a mixture of hexane and ethyl acetate to give 2-[1-hydroxy-1-(3-methoxyphenyl)-2,2,2-trifluoroethyl]thiazole as a pale brown solid (1.56 g), m.p. 88°–92° C.

Boron tribromide (1.5 ml) was added dropwise to a mixture of the product so obtained (1.56 g) and methylene chloride (20 ml) which had been cooled to −70° C. The mixture was allowed to warm to ambient temperature and was stirred for Z hours. A saturated aqueous sodium bicarbonate solution was added careiully until there was no further effervescence and the mixture was extracted with methylene chloride (3×30 ml). The combined extracts were washed with water and with a saturated sodium chloride solution dried (MgSO₄) and evaporated to give 2-[1-hydroxy-1-(3-hydroxyphenyl)-2,2,2-trifluoroethyl]thiazole as a yellow solid (0.74 g), m.p. 133°–135° C.

EXAMPLE 9

Using a similar procedure to that described in Example 1, except that the appropriate alkylating agent was used in place of 3-bromomethyl-1,2-dihydro-1-methyl-quinolin-2-one and the appropriate thiazole was used, there were thus obtained the compounds described in the following table:

TABLE III

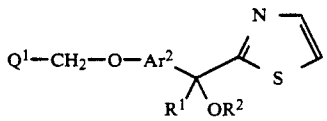

| Ex. 9 Compd. No. | Q¹ | Ar² | R¹ | R² | Yield (%) | m.p. (°C.) |
|---|---|---|---|---|---|---|
| 1[a] | 1,2-dihydro-1-methyl-2-oxoquinolin-3-yl | 5-fluoro-1,3-phenylene | Et | Me | 70 | 131–134 |

TABLE III-continued

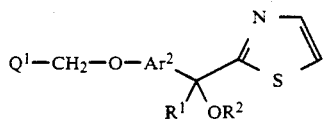

| Ex. 9 Compd. No. | Q¹ | Ar² | R¹ | R² | Yield (%) | m.p. (°C.) |
|---|---|---|---|---|---|---|
| 2[b] | 1,2-dihydro-2-oxo-quinolin-3-yl | 5-fluoro-1,3-phenylene | Et | Me | 34 | 201-204 |
| 3[c] | 1,2-dihydro-1-methyl-2-oxoquinolin-6-yl | 1,3-phenylene | Et | Me | 91 | 90-92 |
| 4[d] | 1,2-dihydro-6-fluoro-1-methyl-2-oxoquinolin-3-yl | 1,3-phenylene | Et | Me | 69 | 134-135 |
| 5[e] | 2-quinazolinyl | 1,3-phenylene | Et | Me | 82 | 78 |
| 6[f] | 4-chloro-2-methyl-quinolin-6-yl | 1,3-phenylene | Et | Me | 55 | 128-129 |
| 7[g] | 1,2-dihydro-1-(2-dimethylaminoethyl)-2-oxoquinolin-3-yl | 1,3-phenylene | Et | Me | 59 | 105 |
| 8[h] | 6-quinoxalinyl | 3,5-pyridylene | Et | Me | 30 | oil |

Notes a. The product was recrystallised from a mixture of hexane and acetone.

The thiazole starting material was obtained as follows:

Benzyl alcohol (10 ml) was added to a slurry of sodium hydride(55% w/w dispersion in mineral oil, 4.4 g) in dimethylformamide(180 ml) and the mixture was stirred at ambient temperature for 1 hour. 3,5-Difluorobromobenzene (17.7 g) was added and the mixture was stirred at ambient temperature for 3 hours. The mixture was evaporated and the residue was partitioned between diethyl ether and water. The organic layer was washed with water, dried (MgSO₄) and evaporated. There was thus obtained 3-benzyloxy-5-fluorobromobenzene (24 g; b.p. 120°-124° C. at 0.1 mm Hg).

A solution of a portion (1.4 g) of the product so obtained in tetrahydrofuran (20 ml) was cooled to −70° C. and n-butyl-lithium (1.6M in hexane, 3.1 ml) was added. The mixture was stirred at −70° C. for 5 minutes and then a solution of ethyl 2-thiazolyl ketone (0.7 g; *Bull. Soc. Chim. France,* 1962, 2072) in tetrahydrofuran (3 ml) was added. The mixture was stirred and allowed to warm to ambient temperature. Vater (1 ml) was added and the mixture was evaporated. Water (50 ml) was added, the mixture was neutralised by the addition of acetic acid and a diethyl ether extract was taken. The organic extract was washed with water, dried (MgSO₄) and evaporated. The residue was purified by column chromatography using a 3:1 v/v mixture of hexane and ethyl acetate as eluent. There was thus obtained 2-[1-(3-benzyloxy-5-fluorophenyl)-1-hydroxypropyl]thiazole (0.9 g, 53%), m.p. 78°-80° C. (recrystallised from a mixture of hexane and acetone).

A mixture of the product so obtained, sodium hydride (50% w/w dispersion in mineral oil, 0.126 g) and dimethylformamide (3 ml) was stirred at ambient temperature for 5 minutes and then cooled to 0° C. in an ice bath. Methyl iodide (0.5 ml) was added and the mixture was stirred at ambient temperature for 10 minutes, poured into water, neutralised by the addition of 2N aqueous hydrochloric acid solution and extracted with diethyl ether. The organic layer was washed with water, dried (MgSO₄) and evaporated. There was thus obtained 2-[1-(3-benzyloxy-5-fluorophenyl)-1-methoxypropyl]thiazole (0.79 g), as an oil.

NMR Spectrum (CDCl₃, delta values) 0.75(t, 3H), 2.3-2.7(m, 2H), 3.2(s, 3H), 5.0(s. 2H), 6.5-7.4(m, 9H), 7.7(d, 1H).

A mixture of a portion (0.2 g) of the product so obtained, 50% palladium-on-charcoal catalyst (0.4 g) and ethyl acetate (3 ml) was stirred under an atmosphere of hydrogen for 1.5 hours. The mixture was filtered and the filtrate was evaporated. There was thus obtained the required starting material (0.13 g), m.p. 168°-170° C. (recrystallised from diethyl ether).

b. The product was recrystallised from a mixture of dimethylformamide and water.

c. The 6-bromomethyl-1,2-dihydro-1-methylquinolin-2-one, used as a starting material, was obtained as follows:

A mixture of 1,2-dihydro-1,6-dimethylquinolin-2-one (4.4 g; *Helv. Chim. Acta.,* 1970, 53, 1903), N-bromosuccinimide (4.53 g), azobisisobutyronitrile (0.01 g) and carbon tetrachloride (75 ml) was heated to reflux for 3 hours and illuminated with the light from a 275 watt lamp. The mixture was filtered and the filtrate was evaporated. The residue was partitioned between ethyl acetate and water. The organic phase was washed with water, dried (MgSO₄) and evaporated. The residue was purified by column chromatography using a 2:1 v/v mixture of toluene and ethyl acetate as eluent. There was thus obtained the required starting material (4.8 g, 75%), as a solid, m.p. 107°-108° C. NMR Spectrum (CDCl₃, delta values) 3.7(s, 3H), 4.57(s, 2H), 6.7-7.5(d, 1H), 7.25-7.65(m, 4H).

d. The 3-bromomethyl-6-fluoro-1,2-dihydro-1-methylquinolin-2-one, used as a starting material, was obtained as follows:

Triethylamine (18.2 g) and propionyl chloride (16.7 g) were added in turn to a solution of 4-fluoroaniline (20 g) which had been cooled to 0° C. The mixture was stirred at 5° C. for 1 hour and partitioned between methylene chloride and water. The organic layer was washed with water, dried (MgSO₄) and evaporated to give 4-fluoropropionanilide (29.1 g).

Phosphorus oxychloride (50 3 ml) was added dropwise to dimethylformamide (11.2 ml) which was stirred and cooled to −5° C. As a white solid began to form the mixture was cooled to −15° C. and the phosphorus oxychloride was added more quickly. The white slurry so formed was stirred and allowed to warm to ambient temperature, and then stirred at ambient temperature for 30 minutes. A portion (15 g) of the 4-fluoropropionaldehyde obtained above was added portionwise and the mixture was heated to 75° C. for 6 hours. The mixture was poured onto ice and extracted with ethyl acetate. The organic layer was washed with a saturated aqueous sodium chloride solution, dried (MgSO₄) and evaporated. The residue was purified by column chromatography using toluene as eluent. There was thus obtained 2-chloro-6-fluoro-3-methylquinoline (1 g, 5%), as a solid.

NMR Spectrum (CDCl₃, delta values) 2.54(s, 3H), 7.32–7.49(m, 2H), 7.91(s, 1H), 7.98(m, 1H).

After appropriate repetition of the above reaction steps, a mixture of the quinoline so obtained (10 g), 2N aqueous hydrochloric acid (110 ml) and ethanol (110 ml) was heated to 80° C. for 9 hours. The mixture was poured into water and the precipitate was filtered off and dried in vacuo at 50° C. There was thus obtained 6-fluoro-1,2-dihydro-1-methylquinolin-2-one (7.9 g, 87%).

NMR Spectrum (CDCl₃, delta values) 2.3(s, 3H), 7.18(d, 1H), 7.2(m, 1H), 7.4(d of d,s, 1H), 7.6(s, 1H), 12.34(broad hump, 1H).

Sodium hydride (55% w/w dispersion in mineral oil; 0.775 g) was added portionwise to a solution oi a portion (3 g) of the product so obtained in dimethylformamide (80 ml) which had been cooled to 0° C. and the mixture was stirred at 5° C. for 40 minutes. Methyl iodide (2.65 g) was added dropwise and the mixture was stirred at 5° C. for 1 hours and then allowed to warm to ambient temperature. The mixture was poured into water (100 ml) and the precipitate was filtered off and dried in vacuo at 50° C. There was thus obtained 6-fluoro-1,2-dihydro-1,3-dimethylquinolin-2-one (2.5 g, 78%), m.p. 132° C.

A mixture of a portion (2 g) of the product so obtained, N-bromosuccinimide (1.86 g), azobisisobutyronitrile (0.01 g) and carbon tetrachloride (50 ml) was heated to reflux for 1.5 hours and illuminated with the light from a 275 watt lamp. The mixture was evaporated and the residue was partitioned between methylene chloride and water. The organic phase was washed with water, dried (MgSO₄) and evaporated. The residue was triturated in toluene to give the required starting material (2 g, 71%), m.p. 212° C.

e. 2-Chloromethylquinazoline, used as a starting material, is described in *J. Chem. Soc.*, 1966, 238.

f. 6-Bromomethyl-4-chloro-2-methylquinoline, used as a starting material, is described in European Patent Application No. 0318225 (Example 1 thereof).

g. The 3-bromomethyl-1,2-dihydro-1-(2-dimethylaminoethyl)quinolin-2-one hydrobromide, used as a starting material, was obtained as follows:

Sodium hydride (55% w/w dispersion in mineral oil; 2.8 g) was added portionwise to a suspension of 1,2-dihydro-2-oxoquinoline-3-carbaldehyde (5.19 g) in dimethylformamide (90 ml) and the mixture was stirred at ambient temperature for I hour. 2-Dimethylaminoethyl chloride hydrochloride (4.8 g) was added and the mixture was heated to 60° C. for 3 hours. The mixture was filtered and partitioned between methylene chloride and water. The organic layer was washed with water, dried (MgSO₄) and evaporated. The residue was purified by column chromatography using a 4:1 v/v mixture of methylene chloride and ethanol as eluent. There was thus obtained 1,2-dihydro-1-(2-dimethylaminoethyl)-2-oxoquinoline-3-carbaldehyde (1.64 g, 22%), m.p. 98°–99° C.

Sodium borohydride (0.285 g) was added portionwise to a solution of the product so obtained in methanol (35 ml) which was cooled in an ice-bath. The mixture was stirred at ambient temperature for 2 hours and then evaporated. A 2N aqueous sodium hydroxide solution (5 ml) was added, followed by sufficient drying agent (MgSO₄) to dry the mixture. The mixture was filtered and evaporated. There was thus obtained 1,2-dihydro-3-hydroxymethyl-1-(2-dimethylaminoethyl)quinolin-2-one (1.48 g, 92%), as a foam.

A mixture of a portion (0.74 g) of the product so obtained and concentrated hydrobromic acid (48% w/v; 10 ml) was heated to 75° C. for 4 hours. The mixture was allowed to cool to ambient temperature, ethanol (10 ml) was added and the mixture was evaporated. The process of adding ethanol and evaporating the mixture so obtained was repeated several iimes to remove the hydrobromic acid. There was thus obtained the required starting material (0.62 g, 53%), m.p. 233°–238° C. (decomposes).

h. The product displayed the following characterisitic NHR signals (CDCl₃, delta values) 0.78(t, 3H), 2.52(m, 2H), 3.24(s, 3H), 5.35(s, 2H), 7.28(m, 1H), 7.47(m, 1H), 7.7–7.85(m, 2H), 8.15–8.25(m, 4H), 8.88(s, 2H).

The 2-[1-(5 hydroxypyrid-3-yl)-1-methoxypropyl]-thiazole, used as a starting material, was obtained as follows:

A solution of benzyl alcohol (12.4 g) in dimethylformamide (20 ml) was added to a slurry of sodium hydride (55% w/w dispersion in mineral oil, 5.25 g) in dimethylformamide (130 ml) and the mixture was stirred at ambient temperature for 1 hour. 3,5-Dibromopyridine (26 g) was added and the mixture was heated to 65° C. for 2 hours. The mixture was cooled to ambient temperature and poured onto a mixture of ice and water. The mixture was extracted with ethyl acetate. The organic phase was washed with dilute aqueous hydrochloric acid solution, with dilute aqueous potassium carbonate solution and with a saturated aqueous sodium chloride solution, dried (MgSO₄) and evaporated. There was thus obtained 5-benzyloxy-3-bromopyridine (15.8 g, 55%), as an oil which was used without further purification.

A solution of a portion (5.28 g) of the product so obtained in tetrahydrofuran (100 ml) was cooled to −100° C. and n-butyl-lithium (1.6M in hexane, 12.5 ml) was added dropwise. The mixture was stirred at −100° C. for 5 minutes and then a solution of ethyl 2-thiazolyl ketone (2.82 g) was added. The mixture was stirred and allowed to warm to ambient temperature. A saturated aqueous ammonium chloride solution (100 ml) was added and the mixture was extracted with ethyl acetate. The organic layer was washed with water, dried (MgSO₄) and evaporated. The residue was purified by column chromatography using a 1:1 v/v mixture of hexane and ethyl acetate as eluent. There was thus obtained 2-[1-(5-benzyloxypyrid-3-yl)-1-hydroxypropyl]-thiazole (4.92 g, 75%), as an oil.

NMR Spectrum (CDCl₃, delta values) 0.89(t, 3H), 2.39(m, 2H), 4.4–4 6(broad s, 1H), 5.07(s, 2H), 7.2–7.4(m, 6H), 7.6–8.5(m, 4H).

A mixture of a portion (1.63 g) of the product so obtained, sodium hydride (50% w/w dispersion in oil, 0.24 g) and dimethylformamide (25 ml) was stirred at −8° C. for 30 minutes. Methyl iodide (0.71 g) was added and the mixture was stirred at −5° C. for 1 hour, poured into a mixture of ice and water and extracted with ethyl acetate (3×25 ml). The combined extracts were washed with water, dried (MgSO$_4$) and evaporated. There was thus obtained 2-[1-(5-benzyloxypyrid-3-yl)-1-methoxypropyl]thiazole as an oil (1.6 g).

NMR Spectrum (CDCl$_3$, delta values) 0.77 (t, 3H), 2.45 (m, 1H), 2.68 (m, 1H), 3.2 (s, 3H), 5.1 (s, 2H), 7.3 (m, 6H), 7.7 (d, 1H), 8.0 (s, 1H), 8.3 (broad d, 2H).

A mixture of the product so obtained (1.5 g), 30% palladium-on-charcoal catalyst (1:1 w/w mixture with water, 1.5 g) and ethyl acetate (30 ml) was stirred under an atmosphere of hydrogen for 4 hours. The mixture was filtered. The filtrate was washed with water, dried (MgSO$_4$) and evaporated. There was thus obtained 2-[1-(5-hydroxypyrid-3-yl)-1-methoxypropyl]thiazole as a white solid (0.78 g), m.p. 133°–135° C.

EXAMPLE 10

The reaction described in Example 5 was repeated except that 4-iodopyridine (*J. Chem. Soc.*, 1953, 3232) was used in place of 2-iodopyridine. There was thus obtained 2-[1-[3-(3-(4-pyridyl)prop-2-yn-1-yloxy)-phenyl]-1-methoxypropyl]thiazole in 78% yield, as an oil.

NMR Spectrum (CDCl$_3$, delta values) 0.8(t, 3H), 2.55(m, 2H), 3.2(s, 3H), 4.9(s, 2H), 6.9–7.7(m, 10H).

EXAMPLE 11

The reaction described in Example 5 was repeated except that 1-iodoisoquinoline (*Chem. Pharm. Bull. Jap.*, 1982, 30, 1731) was used in place of 2-iodopyridine. There was thus obtained 2-[1-[3-(3-(1-isoquinolyl)-prop-2-yn-1-yloxy)phenyl]-1-methoxypropyl]thiazole in 48% yield, m.p. 73°–75° C.

EXAMPLE 12

The reaction described in Example 5 was repeated except that 2-[1-[3-methoxy-4-(2-propynyloxy)phenyl]-1-methoxypropyl]thiazole was used in place of 2-[1-(3-(2-propynyloxy)phenyl)-1-methoxypropyl]thiazole and that the reaction mixture was stirred at ambient temperature for 16 hours. There was thus obtained 2-[1-[3-methoxy-4-(3-(2-pyridyl)prop-2-yn-1-yloxy)phenyl]-1-methoxypropyl]thiazole in 41% yield, as an oil.

NMR Spectrum (CDCl$_3$, delta values) 0.8(t, 3H), 2.4(m, 1H), 2.7(m, 1H), 3.2(s, 3H), 3.85(s, 3H), 5.0(s, 2H), 7.0(m, 3H), 7.25(m, 2H), 7.4(d, 1H), 7.65(d, 1H), 7.7(d, 1H), 8.6(d, 1H).

The 2-[1-[3-methoxy-4 (2-propynyloxy)phenyl]-1-methoxypropyl]thiazole, used as a starting material, was obtained as follows:

Tert-butyldimethylsilyl chloride (14 g) was added to a mixture of ethyl vanillate (15 g), imidazole (13 g) and tetrahydrofuran (100 ml) and the mixture was stirred at ambient temperature for 48 hours. The mixture was filtered and evaporated to give ethyl 4-(tert-butyldimethylsilyloxy)-3-methoxybenzoate (25.1 g). A solution of the product so obtained in tetrahydrofuran (50 ml) was cooled to −70° C. and to this was added a cooled (−70° C.) solution of thiazol-2-yl-lithium prepared by adding 2-bromothiazole (14.1 g) to a mixture of n-butyl-lithium (1.5M in hexane, 57.3 ml) and diethyl ether (30 ml) which had been cooled to −70° C. The mixture was stirred for 16 hours and allowed to warm to ambient temperature. The mixture was poured into a saturated aqueous ammonium chloride solution and extracted with ethyl acetate (3×100ml). The combined extracts were washed with water and with a saturated aqueous sodium chloride solution, dried (MgSO$_4$) and evaporated. The residue was purified by column chromatography using increasingly polar mixtures of methylene chloride and ethyl acetate as eluent. There was thus obtained 4-hydroxy-3-methoxyphenyl 2-thiazolyl ketone (4.5 g) in 24% yield, m.p. 103° C.

The product so obtained (4.0 g) was reacted with tert-butyldimethylsilyl chloride using the procedure described immediately above to give 4-tert-butyldimethylsilyloxy-3-methoxyphenyl 2-thiazolyl ketone (6.5 g). A solution of a portion of the ketone so obtained (5.9 g) in tetrahydrofuran (5 ml) was added to a diethyl ether solution of ethylmagnesium iodide [prepared from iodoethane (2.8 ml) and magnesium (0.816 g) under diethyl ether (10 ml)] and the mixture was heated to reflux for 15 minutes. The mixture was poured into a saturated aqueous ammonium chloride solution and extracted with ethyl acetate (3×25 ml). The combined extracts were washed with water (2×50 ml), with a saturated aqueous sodium chloride solution, dried (MgSO$_4$) and evaporated. There was thus obtained 2-[1-(4-tert-butyldimethylsilyloxy-3-methoxyphenyl)-1-hydroxypropyl]thiazole (5.8 g).

The product so obtained was reacted with methyl iodide using the procedure described in Example 1 except that the product was purified by column chromatography using increasingly polar mixtures of methylene chloride and ethyl acetate as eluent. There was thus obtained 2-[1-(4-tert-butyldimethylsilyloxy-3-methoxyphenyl)-1-methoxypropyl]thiazole (3 g).

Tetra-n-butylammonium fluoride (1M in tetrahydrofuran; 16 ml) was added over 5 minutes to a solution of the product so obtained in tetrahydrofuran (50 ml). The mixture was poured into a saturated aqueous ammonium chloride solution and extracted with ethyl acetate (3×70 ml). The combined extracts were washed with water, with a saturated aqueous sodium chloride solution, dried (MgSO$_4$) and evaporated. There was thus obtained 2-[1-(4-hydroxy-3-methoxyphenyl)-1-methoxypropyl]thiazole (1.3 g), m.p. 127°–129° C. (recrystallised from a mixture of petroleum ether (b.p 60°–80° C.) and methylene chloride).

After repetition of the above reactions, a mixture of the product so obtained (1.8 g), 2-propynyl bromide (80% w/v solution in toluene, 1 ml), potassium carbonate (1.2 g) and dimethylformamide (10 ml) was stirred at ambient temperature for 16 hours. The mixture was partitioned between ethyl acetate and water The organic layer was washed with water and with a saturated aqueous sodium chloride solution, dried (MgSO$_4$) and evaporated. The residue was purified by column chromatography using a 9:1 v/v mixture of methylene chloride and ethyl acetate as eluent. There was thus obtained the required starting material (0.65 g), as a gum.

NMR Spectrum (CDCl$_3$, delta values) 0.8(t, 3H), 2.3–2.5(m, 2H), 2.5(t, 1H), 2.6–2.8(m, 2H), 3.2(s, 3H), 3.8(s, 3H), 4.7(d, 2H), 7.0(m, 3H), 7.25(d, 1H), 7.7(d, 1H).

EXAMPLE 13

Using a similar procedure to that described in Example 8, 3-(2-pyridyl)prop-2-yn-1-yl bromide hydrobromide was reacted with 2-[1-(5-fluoro-3-hydroxyphenyl)-1-methoxypropyl]thiazole to give 2-[1-[5-fluoro-3-(3 (2-pyridyl)prop-2-yn-1-yloxy)phenyl]-1-methoxypropyl]-thiazole in 54% yield, as an oil.

NMR Spectrum (CDCl3, delta values) 0.8(t, 3H), 2.5(m, 2H), 3.2(s, 3H), 4.9(s, 2H), 6.4-7.7(m, 8H), 8.6(d, 1H).

The 3-(2-pyridyl)prop-2-yn-1-yl bromide hydrobromide, used as a starting material, was obtained by repetition of the procedure described in the portion of Example 7 which is concerned with the preparation of starting materials, except that 2-iodopyridine was used in place of 3-iodopyridine. There was thus obtained the required starting material in 7% yield, as a solid salt.

NMR Spectrum (CD3SOCD3) 4.55 (s, 2H), 7.55 (m, 1H), 7.7 (m, 1H), 8.0 (m, 1H), 8.68 (m, 1H).

EXAMPLE 14

Sodium hydride (50% w/w dispersion in mineral oil, 0.29 g) was added portionwise to a solution of 2-[1-(5-hydroxypyrid-3-yl)-1-methoxypropyl]thiazole (0.75 g) in dimethylformamide (20 ml) and the mixture was stirred at ambient temperature for 30 minutes. The mixture was cooled to −10° C. and 3-(2-pyridyl)prop-2-yn-1-yl bromide hydrobromide (0.83 g) was added. The mixture was stirred at −5° C. for hour. The mixture was partitioned between ethyl acetate and water. The organic phase was washed with water, dried (MgSO4) and evaporated. The residue was purified by column chromatography using ethyl acetate as eluent. There was thus obtained 2-[1-[5-(3-(2-pyridyl)prop-2-yn-1-yloxy)pyrid-3-yl]-1-methoxypropyl]thiazole in 28% yield, as an oil.

NMR Spectrum (CDCl3, delta values) 0.8(t, 3H), 2.4-2.7(m, 2H), 3.25(s, 3H), 5.0(s, 2H), 7.2-7.7(m, 7H), 8.32(m, 1H), 8.58(m, 1H).

EXAMPLE 15

Using a similar procedure to that described in Example 1, 2-bromomethylquinoline was reacted with 2-[1-(4-hydroxy-3-methoxyphenyl)-1-methoxypropyl]thiazole to give 2-[1-methoxy-1-[3-methoxy-4-(quinol-2-ylmethoxy)phenyl]propyl]thiazole in 52% yield, m.p. 100°-102° C. (recrystallised from a mixture of petroleum ether (b.p. 60°-80° C.) and methylene chloride).

EXAMPLE 16

Using a similar procedure to that described in Example 1, 3-bromomethyl-1,2-dihydroquinolin-2-one was reacted with 2-[1-(4-hydroxy-3-methoxyphenyl)-1-methoxypropyl]thiazole to give 2-[1-methoxy-1-[3-methoxy-4-(1,2 dihydro-2-oxoquinolin-3ylmethoxy)-phenyl]propyl]thiazole in 28% yield, m.p. 170°-171° C. (recrystallised from a mixture of hexane and ethyl acetate).

EXAMPLE 17

Sodium hydride (0.032 g of a 55% w/w dispersion in mineral oil) was added portionwise to a stirred solution of 2-[1-hydroxy-1-[3-(quinol-2-ylmethoxy)phenyl]-2,2,2-trifluoroethyl]thiazole in tetrahydrofuran (1 ml) and the mixture was stirred at ambient temperature for 10 minutes. A solution of methyl iodide (0.07 ml) in tetrahydrofuran (0.7 ml) was added and the mixture was stirred at ambient temperature for 3 days. The mixture was evaporated and the residue was purified by column chromatography using a 6:1 v/v mixture of toluene and ethyl acetate as eluent. There was thus obtained 2-1-methoxy-1-[3-(quinol-2-ylmethoxy)phenyl]-2,2,2-trifluoroethyl]thiazole (0.2 g, 74%), as an oil.

NMR Spectrum (CD3SOCD3, delta values) 3.3 (s, 3H), 5.4 (s, 2H), 7.1 (m, 1H), 7.2 (m, 1H), 7.4-7.8 (m, 5H), 7.9 (d of d's, 2H), 8.0 (m, 2H), 8.4 (d, 1H).

NMR Spectral Data

For those compounds of the invention within Examples 2 to 7 hereinbefore which were obtained as oils, the following NMR spectral data were obtained:

Example 2, Compound No. 2: (CDCl3, delta values) 0.6-0.7(t, 3H), 2.3-2.7(m, 2H), 3.1(s, 3H), 5.1(s, 2H), 6.9-7.05(m, 3H), 7.2-7.4(m, 2H), 7.5(d, 1H), 7.6-7.7(m, 2H), 7.8(t, 1H), 8.6(m, 1H).

Example 2, Compound No. 6: (CDCl3, delta values) 0.75(t, 3H), 2.32-2.78(m, 2H), 3.2(s, 3H), 5.3(s, 2H), 6.85-8.15(m, 9H), 8.9(s, 2H).

Example 2, Compound No. 12: (CD3SOCD3, delta values) 3.2 (s, 3H), 3.3 (s, 3H), 5.3 (s, 2H), 6.9-8.9 (m, 12H).

Example 3: (CDCl3, delta values) 0.8(t, 3H), 2.35-2.8(m, 2H), 3.2(s, 3H), 4.7(d, 2H), 6.4-6.55(m, 1H), 6.7-6.8(d, 1H), 6.8-6.9(m, 1H), 7.05-7.35(m, 5H), 7.6-7.8(m, 2H), 8.5(d, 1H), 8.6(d, 1H).

Example 4: (CD3SOCD3, delta values) 0.7 (t, 3H), 2.3-2.7 (m, 2H), 3.2 (s, 3H), 4.8 (d, 2H), 6.75-7.05 (m, 5H), 7.1-7.4 (m, 2H), 7.45 (m, 3H), 7.6-7.7 (m, 2H), 7.7-7.8 (m, 1H), 8.5 (m, 1H).

Example 6, Compound No. 1: (CDCl3, delta values) 0.8(t, 3H), 2.4-2.7(m, 2H), 3.2(s, 3H), 4.9(s, 2H), 6.9-7.4(m, 5H), 7.7(d, 1H), 8.5-8.7(m, 3H).

Example 6, Compound No. 3: (CD3SOCD3, delta values) 1.95 (s, 3H), 3.2 (s, 3H), 5.1 (s, 2H), 6.9-7.4 (m, 5H), 7.6-7.7 (m, 2H), 8.6-8.85 (m, 3H).

Example 7: (CDCl3, delta values) 0.75(t, 3H), 2.4-2.8(m, 2H), 3.2(s, 3H), 4.9(s, 2H), 6.9-7.8(m, 8H), 8.5-8.7(m, 2H).

EXAMPLE 18

The following illustrate representative pharmaceutical dosage forms containing the compound of formula I, or a pharmaceutically acceptable salt salt thereof (hereafter compound X), for therapeutic or prophylactic use in humans:

| (a) Tablet I | mg/tablet |
|---|---|
| Compound X | 100 |
| Lactose Ph.Eur | 182.75 |
| Croscarmellose sodium | 12.0 |
| Maize starch paste (5% w/v paste) | 2.25 |
| Magnesium stearate | 3.0 |
| (b) Tablet II | mg/tablet |
| Compound X | 50 |
| Lactose Ph.Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |
| (c) Tablet III | mg/tablet |
| Compound X | 1.0 |
| Lactose Ph.Eur | 93.25 |
| Croscarmellose sodium | 4.0 |
| Maize starch paste (5% w/v paste) | 0.75 |
| Magnesium stearate | 1.0 |
| (d) Capsule | mg/capsule |
| Compound X | 10 |
| Lactose Ph.Eur | 488.5 |
| Magnesium stearate | 1.5 |
| (e) Injection I | (50 mg/ml) |
| Compound X | 5.0% w/v |
| 1M Sodium hydroxide solution | 15.0% v/v |
| 0.1M Hydrochloric acid (to adjust pH to 7.6) | |
| Polyethylene glycol 400 | 4.5% w/v |
| Water for injection to 100% | |

-continued

| (f) Injection II | (10 mg/ml) |
|---|---|
| Compound X | 1.0% w/v |
| Sodium phosphate BP | 3.6% w/v |
| 0.1M Sodium hydroxide solution | 15.0% v/v |
| Water for injection to 100% | |
| (g) Injection III | (1 mg/ml, buffered to pH 6) |
| Compound X | 0.1% w/v |
| Sodium phosphate BP | 2.26% w/v |
| Citric acid | 0.38% w/v |
| Polyethylene glycol 400 | 3.5% w/v |
| Water for injection to 100% | |
| (h) Aerosol I | mg/ml |
| Compound X | 10.0 |
| Sorbitan trioleate | 13.5 |
| Trichlorofluoromethane | 910.0 |
| Dichlorodifluoromethane | 490.0 |
| (i) Aerosol II | mg/ml |
| Compound X | 0.2 |
| Sorbitan trioleate | 0.27 |
| Trichlorofluoromethane | 70.0 |
| Dichlorodifluoromethane | 280.0 |
| Dichlorotetrafluoroethane | 1094.0 |
| (j) Aerosol III | mg/ml |
| Compound X | 2.5 |
| Sorbitan trioleate | 3.38 |
| Trichlorofluoromethane | 67.5 |
| Dichlorodifluoromethane | 1086.0 |
| Dichlorotetrafluoroethane | 191.6 |
| (k) Aerosol IV | mg/ml |
| Compound X | 2.5 |
| Soya lecithin | 2.7 |
| Trichlorofluoromethane | 67.5 |
| Dichlorofluoromethane | 1086.0 |
| Dichlorotetrafluoroethane | 191.6 |

Note
The above formulations may be obtained by conventional procedures well known in the pharmaceutical art. The tablets (a)–(c) may be enteric coated by conventional means, for example to provide a coating of cellulose acetate phthalate. The aerosol formulations (h)–(k) may be used in conjunction with standard, metered dose aerosol dispensers, and the suspending agents sorbitan trioleate and soya lecithin may be replaced by an alternative suspending agent such as sorbitan monooleate, sorbitan sesquioleate, polysorbate 80, polyglycerol oleate or oleic acid.

CHEMICAL FORMULAE

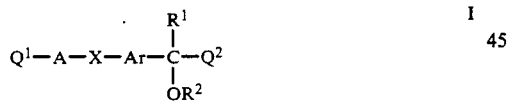

I

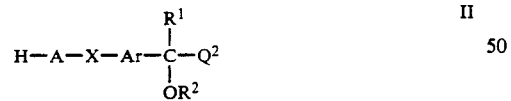

II

III

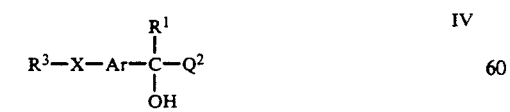

IV

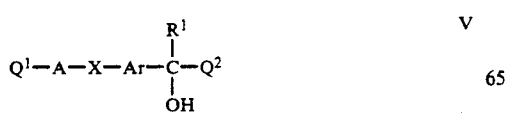

V

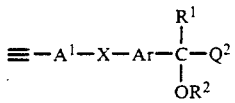

VI

What we claim is:

1. A thiazole of the formula I

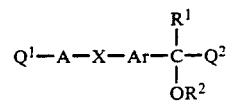

I wherein $Q^1$ is pyridyl which may optionally bear one, two or three substituents selected from halogeno, hydroxy, oxo, cyano, (1–4C)alkyl, (1–4C)alkoxy, fluoro-(1–4C)alkyl, (1–4C)alkylamino-(1–4C)alkyl and di-[(1–4C)alkyl]amino-(1–4C)alkyl; wherein A is (1–6C)alkylene, (3–6C)alkenylene, (3–6C)alkynylene or cyclo(3–6C)alkylene;

wherein X is oxy, thio, sulphinyl, sulphonyl or imino;

wherein Ar is phenylene which may optionally bear one or two substituents selected from halogeno, hydroxy, amino, nitro, carboxy, cyano, carbamoyl, (1–4C)alkyl, (1–4C)alkoxy, (1–4C)alkylthio, (1–4C)alkylsulphinyl, (1–4C)alkylsulphonyl, (1–4C)alkylamino, di-[(1–4C)alkyl]amino, (1–4C)alkoxycarbonyl, N-[(1–4C)alkyl]carbamoyl, N,N-di-[(1–4C)alkyl]carbamoyl, (2–4C)alkanoylamino, hydroxy-(2–4C)alkoxy, (1–4C)alkoxy-(2–4C)alkoxy, amino-(2–4C)alkoxy, cyano-(1–4C)alkoxy, carbamoyl-(1–4C)alkoxy, N-[(1–4C)alkyl]carbamoyl-(1–4C)alkoxy, N,N-di-[(1–4C)alkyl]carbamoyl-(1–4C)alkoxy, (1–4C)alkylamino-(2–4C)alkoxy, di-[(1–4C)alkyl]amino-(2–4C)alkoxy, (1–4C)alkoxycarbonyl-(1–4C)alkoxy, fluoro-(1–4C)alkyl, hydroxy-(1–4C)alkyl, amino-(1–4C)alkyl, cyano-(1–4C)alkyl, (1–4C)alkoxy-(1–4C)alkyl, (1–4C)alkylamino-(1–4C)alkyl, di-[(1–4C)alkyl]amino-(1–4C)alkyl and (2–4C)alkanoylamino-(1–4C)alkyl, or Ar is 2,4-, 2,5-, 3,5- or 2,6-pyridylene, 2,4-, 2,5- or 4,6-pyrimidinylene, 3,5- or 3,6-pyridazinylene or 2,5- or 2,6-pyrazinylene which may optionally bear one or two substituents selected from halogeno, hydroxy, amino, cyano, (1–4C)alkyl, (1–4C)alkoxy, (1–4C)alkylamino and di[(1–4C)alkyl]amino;

wherein $R^1$ is (1–6C)alkyl, (2–6C)alkenyl, (2–6C)alkynyl, fluoro(1–4C)alkyl, cyano(1–4C)alkyl, hydroxy-(1–4C)alkyl, (1–4C)alkoxy(1–4C)alkyl and (2–4C)alkanoyloxy-(1–4C)alkyl;

wherein $R^2$ is hydrogen, (1–6C)alkyl, (3–6C)alkenyl, (3–6C)alkynyl, (1–4C)alkoxycarbonyl-(1–4C)alkyl, carboxy-(1–4C)alkyl, carbamoyl-(1–4C)alkyl, cyano(1–4C)alkyl or (2–4C)alkanoyl or $R^2$ is benzoyl which may optionally bear a substituent selected from halogeno, (1–4C)alkyl and (1–4C)alkoxy; and wherein $Q^2$ is thiazolyl which may optionally bear one or two substituents selected from halogeno, amino, nitro, cyano, carbamoyl, (1–4C)alkyl, (1–4C)alkoxy, (1–4C)alkylamino, di-[(1–4C)alkyl]amino, (1–4C)alkoxycarbonyl, N-[(1–4C)alkyl]carbamoyl, N,N-di-[(1–4C)alkyl]carbamoyl, (2–4C)alkanoylamino, fluoro-(1–4C)alkyl and hydroxy-(1–4C)alkyl; or a pharmaceutically-acceptable salt thereof.

2. A thiazole of the formula I as claimed in claim 1 wherein $Q^1$ is pyridyl which may optionally bear one, two or three substituents selected from fluoro, chloro, hydroxy, oxo, methyl, ethyl, methoxy, trifluoromethyl, 2-fluoroethyl and 2-dimethylaminoethyl;
   wherein A is methylene, 1-propenylene or 1-propynylene;
   wherein X is oxy;
   wherein Ar is 1,3-phenylene or 1,4-phenylene which may optionally bear one substituent selected from fluoro, chloro, hydroxy, amino, nitro, methyl, methoxy and trifluoromethyl, or Ar is 3,5-pyridylene;
   wherein $R^1$ is methyl or ethyl;
   wherein $R^2$ is hydrogen, methyl, ethyl or allyl; and $Q^2$ is 2-thiazolyl;
or a pharmaceutically acceptable salt thereof.

3. A thiazole of the formula I as claimed in claim 1 wherein $Q^1$ is 2-pyridyl or, 3-pyridyl which may optionally bear one substituent selected from chloro, hydroxy, cyano, methyl, methoxy and trifluoromethyl;
   wherein A is methylene, ethylene, trimethylene, 1-propenylene, 2-methylprop-1-enylene or 1-propynylene;
   wherein X is oxy;
   wherein Ar is 1,3-phenylene or 1,4-phenylene which may optionally bear one substituent selected from chloro, bromo, hydroxy, amino, nitro, methyl, methoxy, methylthio, methylsulphinyl, methylsulphonyl, methylamino, dimethylamino, trifluoromethyl, acetamido, cyanomethoxy and carbamoylmethoxy;
   wherein Ar is 2,4-, 2,5-, 3,5- or 2,6-pyridylene or 4,6-pyrimidinylene which may optionally bear one substituent selected from chloro, methyl and methoxy;
   wherein $R^1$ is, methyl, ethyl, propyl, vinyl, ethynyl, 1-propynyl, trifluoromethyl, hydroxymethyl, methoxymethyl or acetoxymethyl;
   wherein $R^2$ is hydrogen, methyl, ethyl, allyl, 2-propynyl or cyanomethyl; and
   wherein $Q^2$ is 2-thiazolyl;
or a pharmaceutically-acceptable salt thereof.

4. A thiazole of the formula I as claimed in claim 1 wherein $Q^1$ is 2-pyridyl, 3-pyridyl or, 4-pyridyl,
   wherein A is 1-propenylene or 1-propynylene;
   wherein X is oxy;
   wherein Ar is 1,3-phenylene or 1,4-phenylene which may optionally bear one substituent selected from fluoro and methoxy, or Ar is 3,5-pyridylene;
   wherein $R^1$ is methyl or ethyl;
   wherein $R^2$ is methyl; and
   wherein $Q^2$ is 2-thiazolyl;
or a pharmaceutically-acceptable salt thereof.

5. A thiazole of the formula I as claimed in claim 1, or a pharmaceutically-acceptable salt thereof, selected from the group consisting of,
2-[1-[3-(3-(2-pyridyl)prop-2-yn-1-yloxy)phenyl]-1-methoxypropyl]thiazole,
2-[1-[3-(3-(3-pyridyl)prop-2-yn-1-yloxy)phenyl]-1-methoxypropyl]thiazole,
2-[1-[3-(3-(3-pyridyl)propy-2-yn-1-yloxy)phenyl]-1-methoxyethyl]thiazole,
2-[1-[5-fluoro-3-(3-(2-pyridyl)prop-2-yn-1-yloxy)-phenyl]-1-methoxypropyl]thiazole.

6. A pharmaceutical composition which comprises a thiazole of the formula I, or a pharmaceutically-acceptable salt thereof, as claimed in any one of claims 3, 4, 6 or 1 in association with a pharmaceutically-acceptable diluent or carrier.

7. A thiazole of the formula I, or a pharmaceutically-acceptable salt thereof, as claimed in any one of claims 3, 4, 6 or 1 for use in a method of treatment of the human or animal body by therapy.

8. A method of treating a disease or medical condition mediated alone or in part by one or more leukotrienes which comprises administering to a warm-blooded animal requiring such treatment an effective amount of a thiazole of the formula I, or a pharmaceutically-acceptable salt thereof, as claimed in claims 3, 4, 6 or 1.

* * * * *